United States Patent
Hulmann-Cottier et al.

(10) Patent No.: US 8,697,074 B2
(45) Date of Patent: *Apr. 15, 2014

(54) METHODS AND COMPOSITIONS FOR ENHANCED DELIVERY OF MACROMOLECULES

(75) Inventors: Valerie Hulmann-Cottier, Zurich (CH); David Urech, Hombrechtikon (CH); Esther Furrer, Forch (CH)

(73) Assignee: ESBATech, an Alcon Biomedical Research Unit LLC (CH)

( * ) Notice: Subject to any disclaimer, the term of this patent is extended or adjusted under 35 U.S.C. 154(b) by 212 days.

This patent is subject to a terminal disclaimer.

(21) Appl. No.: 13/000,533

(22) PCT Filed: Jul. 10, 2009

(86) PCT No.: PCT/CH2009/000248
§ 371 (c)(1),
(2), (4) Date: Dec. 21, 2010

(87) PCT Pub. No.: WO2010/003268
PCT Pub. Date: Jan. 14, 2010

(65) Prior Publication Data
US 2011/0135644 A1  Jun. 9, 2011

Related U.S. Application Data

(60) Provisional application No. 61/079,586, filed on Jul. 10, 2008.

(51) Int. Cl.
*A61K 39/395* (2006.01)
*C12P 21/08* (2006.01)

(52) U.S. Cl.
USPC .................................. 424/135.1; 530/387.3

(58) Field of Classification Search
None
See application file for complete search history.

(56) References Cited

U.S. PATENT DOCUMENTS

| | | | |
|---|---|---|---|
| 5,534,496 A | 7/1996 | Lee et al. | |
| 6,534,633 B1 * | 3/2003 | Weidanz et al. | 530/387.3 |
| 6,803,438 B1 | 10/2004 | Brocchini et al. | |
| 7,045,337 B2 | 5/2006 | Schultz et al. | |
| 7,083,970 B2 | 8/2006 | Schultz et al. | |
| 7,431,927 B2 * | 10/2008 | Couto et al. | 424/145.1 |
| 8,293,235 B2 * | 10/2012 | Borras et al. | 424/133.1 |
| 2004/0156824 A1 | 8/2004 | Epstein | |
| 2007/0092940 A1 | 4/2007 | Eigenbrot et al. | |

FOREIGN PATENT DOCUMENTS

| | | |
|---|---|---|
| EP | 1210093 A1 | 6/2002 |
| EP | 1461369 A2 | 7/2003 |
| EP | 1496941 A1 | 10/2003 |
| EP | 1222217 B1 | 6/2005 |
| EP | 1240337 B1 | 8/2006 |
| EP | 1701741 B1 | 5/2008 |
| EP | 1648518 B1 | 8/2009 |
| WO | 03059973 A2 | 7/2003 |
| WO | 03089010 A1 | 10/2003 |
| WO | 03097697 A2 | 11/2003 |
| WO | 03098991 A2 | 12/2003 |
| WO | 2004031400 A2 | 4/2004 |
| WO | 2005007197 A2 | 1/2005 |
| WO | 2005065712 A2 | 7/2005 |
| WO | 2006131013 A2 | 12/2006 |
| WO | 2008006235 A2 | 1/2008 |
| WO | 2009000098 A2 | 12/2008 |
| WO | 2009058957 A2 | 5/2009 |
| WO | 2009155723 A2 | 12/2009 |
| WO | 2009155726 A2 | 12/2009 |
| WO | 2010003268 A2 | 1/2010 |
| WO | 2010006454 A2 | 1/2010 |

OTHER PUBLICATIONS

Vickers. A vaccine against Alzheimer's disease: developments to date. Drugs Aging 2002; 19(7):487-94.*
Skerra and Pluckthun; "Assembly of a functioanl immunoglobulin Fv fragment in *Escherichia coli*"; Science; vol. 240; pp. 1038-1041 (May 20, 1988).
Trolle et al; "Intranasal immunization with protein-linked phosphorylcholine protects mice against a lethal intranasal challenge with *Streptococcus pneumoniae*"; Vaccine; vol. 18; pp. 2991-2998 (2000).
Ward et al; "Binding activities of a repertoire of single immunoglobulin variable domains secreted form *Escherichia coli*"; Letters to Nature; vol. 341; pp. 544-546 (Oct. 12, 1989).
Yen and Lee; "Penetration enhancemetn effect of Pz-peptide, a paracellularly transported peptide, in rabbit intestinal segments and Caco-2 cell monolayers"; Journal of Controlled Release; vol. 36; pp. 25-37 (1995).
Alfthan et al.; "Properties of a single-chain antibody containing different linker peptides"; Protein Engineering; vol. 8; No. 7; pp. 725-731 (1995).
Berge et al.; "Pharmaceutical salts" Review Article; Journal of Pharmaceutical Sciences; vol. 66; No. 1; pp. 2-19 (Jan. 1977).
Binz and Pluckthun; "Engineered proteins as specific binding reagents"; Current Opinion in Biotechnology; vol. 16; pp. 459-469 (2005).
Bird et al; "Single-chain antigen-binding proteins"; Science; vol. 242; pp. 423-426; (Oct. 21, 1988).
Brummell et al; "Probing the combining site of an anti-carbohydrate antibody by saturation-mutagenesis: role of the heavy-chain CDR3 residues"; Biochemistry; vol. 32; pp. 1180-1187 (1993).
Burks et al; "In vitro scanning saturation mutagenesis of an antibody binding pocket"; Proc. Natl. Acad. Sci.; vol. 94; pp. 412-417 (Jan. 1997).

(Continued)

Primary Examiner — Gregory S Emch

(57) ABSTRACT

The invention provides compositions and methods that enhance the delivery of large macromolecules (i.e., greater than 10 kDa), such as antigen-binding polypeptides, across tight junctions. Such methods and compositions are particularly useful for delivering therapeutic antigen-binding polypeptides to the CNS, via intranasal administration, for the treatment of neurological disorders.

15 Claims, 4 Drawing Sheets

(56) References Cited

OTHER PUBLICATIONS

Choi et al; "Recombinant chimeric OKT3 scFv IgM antibodies mediate immune suppression while reducing T cell activation in vitro"; Eur. J. immunol.; vol. 31; pp. 94-106 (2001).
Dumoulin et al; "Single-domain antibody fragments with high conformational stability"; Protein Science; vol. 11; pp. 500-515 (2002).
Eyles et al; "Immunological responses to nasal delivery of free and encapsulated tetanus toxoid: studies on the effect of vehicle volume"; International Journal of Pharmaceutics; vol. 189; pp. 75-79 (1999).
Furrer et al.; "Pharmacokinetics and posterior segment biodistribution of ESBA105, an anti-TNF-alpha single-chain antibody, upon topical administration of the rabbit eye"; Investigative Ophthalmology & Visual Science; vol. 50; No. 2; pp. 771-778 (2009).
Genbank Acession No. NP_000475.1.
Genbank Acession No. NP_000515.2.
Genbank Acession No. NP_000675.1.
Genbank Acession No. NP_000729.2.
Genbank Acession No. NP_000730.1.
Genbank Acession No. NP_000731.1.
Genbank Acession No. NP_000732.2.
Genbank Acession No. NP_000781.1.
Genbank Acession No. NP_000785.1.
Genbank Acession No. NP_000786.1.
Genbank Acession No. NP_000787.2.
Genbank Acession No. NP_000788.2.
Genbank Acession No. NP_000789.1.
Genbank Acession No. NP_000823.4.
Genbank Acession No. NP_000824.1.
Genbank Acession No. NP_000825.2.
Genbank Acession No. NP_000826.2.
Genbank Acession No. NP_000827.2.
Genbank Acession No. NP_000828.1.
Genbank Acession No. NP_000852.1.
Genbank Acession No. NP_000889.3.
Genbank Acession No. NP_001034.1.
Genbank Acession No. NP_001516.2.
Genbank Acession No. NP_001517.2.
Genbank Acession No. NP_597702.2.
Genbank Acession No. NP_619635.1.
Genbank Acession No. NP_942131.1.
Genbank Acession No. NP_000585.2.
Hamera-Casterman et al; "Naturally occurring antibodies devoid of light chains"; Letters to Nature; vol. 363; pp. 446-448 (Jun. 3, 1993).
Holliger et al; "Diabodies: small bivalent and bispecific antibody fragments"; Proc. Natl. Acad. Sci.; vol. 90; pp. 6444-6448 (Jul. 1993).
Hu et al; "Minibody: a novel engineered anti-carcinoembryonic antigen antibody fragment (single-chain Fv-CH3) which exhibits reapid, high-level targeting of xenografts"; Cancer Research; vol. 56; pp. 3055-3061 (Jul. 1, 1996).
Houston et al; "Protein engineering of antibody binding sites: recovery of specific activity in an anti-digoxin single-chain Fv analogue produced in *Escherichia coli*"; Proc. natl. Acad. Sci.; vol. 85; pp. 5879-5883 (Aug. 1988).
Kipriyanov et al; "Bispecific tandem diabody for tumor therapy with improved antigen binding and pharmacokinetics"; J. Mol. Biol.; vol. 293; pp. 41-56 (1999).
Klavinskis et al.; "Intranasal immunization with plasmid DNA-lipid complexes elicits mucosal immunity in the female genital and rectal tracts"; The Journal of Immunology; vol. 162; pp. 254-262 (1999).
Kobayashi et al.; "Tryptophan H33 plays an important role in pyrimidine (6-4) pyrimidone photoproduct binding by a high-affinity antibody"; Protein Engineering; vol. 12; No. 10; pp. 879-884 (1999).
Lundholm et al; "Induction of mucosal IgA by a novel jet delivery technique for HIV-1 DNA"; Vaccine; vol. 17; pp. 2036-2042 (1999).
Myers and Miller; "Optimal alignments in linear space"; Comput. Appl. Biosci.; vol. 4; No. 1; pp. 11-17 (1988).
Needleman and Wunsch; "A general method applicable to the search for similarities in the amino acid sequence of two proteins"; J. Mol. Biol.; vol. 48; pp. 443-453 (1970).
Ottiger et al.; "Efficient intraocular penetration of topical anti-TNF-alpha single-chain antibody (ESBA105) to anterior and posterior segment without penetration enhancer"; Invest. Ophthalmol. Vis. Sci.; vol. 50; pp. 779-786 (2009).
Roovers et al.; "In vitro characterisation of a monovalent and bivalent form of a fully human anti Ep-CAM phage antibody"; Cancer Immunol. Immunother; vol. 50; pp. 51-59 (2001).

* cited by examiner

SEQUENCE LISTING

<160> NUMBER OF SEQ ID NOS: 37

<210> SEQ ID NO 1
<211> LENGTH: 247
<212> TYPE: PRT
<213> ORGANISM: Artificial Sequence
<220> FEATURE:
<223> OTHER INFORMATION: ESBA105 scFv

<400> SEQUENCE: 1

```
Met Ala Asp Ile Val Met Thr Gln Ser Pro Ser Ser Leu Ser Ala Ser
1               5                   10                  15

Val Gly Asp Arg Val Thr Leu Thr Cys Thr Ala Ser Gln Ser Val Ser
            20                  25                  30

Asn Asp Val Val Trp Tyr Gln Gln Arg Pro Gly Lys Ala Pro Lys Leu
        35                  40                  45

Leu Ile Tyr Ser Ala Phe Asn Arg Tyr Thr Gly Val Pro Ser Arg Phe
    50                  55                  60

Ser Gly Arg Gly Tyr Gly Thr Asp Phe Thr Leu Thr Ile Ser Ser Leu
65                  70                  75                  80

Gln Pro Glu Asp Val Ala Val Tyr Tyr Cys Gln Gln Asp Tyr Asn Ser
                85                  90                  95

Pro Arg Thr Phe Gly Gln Gly Thr Lys Leu Glu Val Lys Arg Gly Gly
            100                 105                 110

Gly Gly Ser Gly Gly Gly Gly Ser Gly Gly Gly Gly Ser Ser Gly Gly
        115                 120                 125

Gly Ser Gln Val Gln Leu Val Gln Ser Gly Ala Glu Val Lys Lys Pro
    130                 135                 140
```

Gly Ala Ser Val Lys Val Ser Cys Thr Ala Ser Gly Tyr Thr Phe Thr
145                 150                 155                 160

His Tyr Gly Met Asn Trp Val Arg Gln Ala Pro Gly Lys Gly Leu Glu
                165                 170                 175

Trp Met Gly Trp Ile Asn Thr Tyr Thr Gly Glu Pro Thr Tyr Ala Asp
            180                 185                 190

Lys Phe Lys Asp Arg Phe Thr Phe Ser Leu Glu Thr Ser Ala Ser Thr
        195                 200                 205

Val Tyr Met Glu Leu Thr Ser Leu Thr Ser Asp Asp Thr Ala Val Tyr
    210                 215                 220

Tyr Cys Ala Arg Glu Arg Gly Asp Ala Met Asp Tyr Trp Gly Gln Gly
225                 230                 235                 240

Thr Leu Val Thr Val Ser Ser
                245

<210> SEQ ID NO 2
<211> LENGTH: 253
<212> TYPE: PRT
<213> ORGANISM: Artificial Sequence
<220> FEATURE:
<223> OTHER INFORMATION: EP34max scFv

<400> SEQUENCE: 2

Glu Ile Val Met Thr Gln Ser Pro Ser Thr Leu Ser Ala Ser Leu Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Ser Gly Lys Ala Pro Lys Leu
        35                  40                  45

Leu Ile Tyr Gln Ala Ser Lys Leu Ala Ser Gly Val Pro Ser Arg Phe
    50                  55                  60

Ser Gly Ser Gly Ser Gly Ala Glu Phe Ser Leu Thr Ile Ser Ser Leu
65                  70                  75                  80

Gln Pro Asp Asp Phe Ala Thr Tyr Tyr Cys Gln Gly Asn Phe Asn Thr
                85                  90                  95

Gly Asp Arg Tyr Ala Phe Gly Gln Gly Thr Lys Leu Thr Val Leu Gly
            100                 105                 110

Gly Gly Gly Gly Ser Gly Gly Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Thr Ala Ser Gly Phe Thr
145                 150                 155                 160

Ile Ser Arg Ser Tyr Trp Ile Cys Trp Val Arg Gln Ala Pro Gly Lys
                165                 170                 175

Gly Leu Glu Trp Val Ala Cys Ile Tyr Gly Asn Asp Ile Thr Pro
            180                 185                 190

Leu Tyr Ala Asn Trp Ala Lys Gly Arg Phe Pro Val Ser Thr Asp Thr
        195                 200                 205

Ser Lys Asn Thr Val Tyr Leu Gln Met Asn Ser Leu Arg Ala Glu Asp
    210                 215                 220

Thr Ala Val Tyr Tyr Cys Ala Arg Leu Gly Tyr Ala Asp Ala Tyr
225                 230                 235                 240

Asp Leu Trp Gly Gln Gly Thr Leu Val Thr Val Ser Ser
                245                 250

```
<210> SEQ ID NO 3
<211> LENGTH: 253
<212> TYPE: PRT
<213> ORGANISM: Artificial Sequence
<220> FEATURE:
<223> OTHER INFORMATION: EP43max scFv

<400> SEQUENCE: 3

Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Phe Pro Ser Arg Phe Ser Gly
50                  55                  60

Ser Gly Ser Gly Ala Glu Phe Thr Leu Thr Ile Ser Gly Leu Glu Pro
65                  70                  75                  80

Ala Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly Gly
                100                 105                 110

Gly Gly Gly Ser Gly Gly Gly Gly Ser Gly Gly Gly Gly Ser Gly Gly
            115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Thr Val Ser Gly Phe Ser Leu
145                 150                 155                 160

Ser Ser Gly Ala Met Ser Trp Val Arg Gln Ala Pro Gly Lys Gly Leu
                165                 170                 175

Glu Trp Val Gly Val Ile Ile Ser Ser Gly Ala Thr Tyr Tyr Ala Ser
            180                 185                 190

Trp Ala Lys Gly Arg Phe Thr Ile Ser Lys Asp Thr Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Arg Gly Gly Pro Asp Asp Ser Asn Ser Met Gly Thr Phe
225                 230                 235                 240

Asp Pro Trp Gly Gln Gly Thr Leu Val Thr Val Ser Ser
                245                 250

<210> SEQ ID NO 4
<211> LENGTH: 250
<212> TYPE: PRT
<213> ORGANISM: Artificial Sequence
<220> FEATURE:
<223> OTHER INFORMATION: ESBA212 scFv

<400> SEQUENCE: 4

Ala Asp Ile Val Leu Thr Gln Ser Pro Ser Ser Leu Ser Ala Ser Val
1               5                   10                  15

Gly Asp Arg Val Thr Leu Thr Cys Arg Ala Ser Ser Ser Val Asn Tyr
                20                  25                  30

Met His Trp Tyr Gln Gln Arg Pro Gly Lys Pro Pro Lys Ala Leu Ile
            35                  40                  45

Tyr Ala Thr Ser Asn Leu Ala Ser Gly Val Pro Ser Arg Phe Ser Gly
50                  55                  60
```

```
Ser Gly Ser Gly Thr Glu Phe Thr Leu Thr Ile Ser Ser Leu Gln Pro
 65                  70                  75                  80

Glu Asp Val Ala Val Tyr Tyr Cys Gln Gln Trp Arg Thr Asn Pro Pro
                 85                  90                  95

Thr Phe Gly Gln Gly Thr Lys Leu Glu Val Lys Arg Gly Gly Gly Gly
            100                 105                 110

Ser Gly Gly Gly Gly Ser Gly Gly Gly Ser Gly Gly Gly Gly Ser
            115                 120                 125

Gln Val Gln Leu Val Gln Ser Gly Pro Glu Val Lys Lys Pro Gly Ala
130                 135                 140

Ser Val Lys Val Ser Cys Thr Ala Ser Gly Tyr Thr Phe Thr Glu Tyr
145                 150                 155                 160

Thr Met His Trp Val Arg Gln Ala Pro Gly Gln Gly Leu Glu Trp Met
                165                 170                 175

Gly Gly Val Asn Pro Tyr Asn Asp Asn Thr Ser Tyr Ile Arg Lys Leu
            180                 185                 190

Gln Gly Arg Val Thr Leu Thr Val Asp Arg Ser Ser Thr Ala Tyr
            195                 200                 205

Met Glu Leu Thr Ser Leu Thr Ser Asp Asp Thr Ala Val Tyr Tyr Cys
210                 215                 220

Ala Arg Tyr Gly Gly Leu Arg Pro Tyr Tyr Phe Pro Met Asp Phe Trp
225                 230                 235                 240

Gly Gln Gly Thr Leu Val Thr Val Ser Ser
                245                 250

<210> SEQ ID NO 5
<211> LENGTH: 253
<212> TYPE: PRT
<213> ORGANISM: Artificial Sequence
<220> FEATURE:
<223> OTHER INFORMATION: ESBA521 scFv

<400> SEQUENCE: 5

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
                20                  25                  30

Tyr Val Ser Trp Tyr Gln Gln Leu Pro Gly Thr Ala Pro Gln Leu Leu
            35                  40                  45

Ile Tyr Asp Asn Thr Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly Gly
            100                 105                 110

Gly Gly Ser Gly Gly Gly Gly Ser Gly Gly Gly Gly Ser Ser Gly
            115                 120                 125

Gly Gly Ser Glu Val Gln Leu Val Glu Ser Gly Gly Gly Leu Val Gln
130                 135                 140

Pro Gly Gly Ser Leu Arg Leu Ser Cys Ala Ala Ser Gly Phe Thr Phe
145                 150                 155                 160

Ser Ser Tyr Ala Met Ser Trp Val Arg Gln Ala Pro Gly Lys Gly Leu
                165                 170                 175

Glu Trp Val Ser Ala Ile Ser Gly Ser Gly Gly Ser Thr Tyr Tyr Ala
```

```
                    180                 185                 190
Asp Ser Val Lys Gly Arg Phe Thr Ile Ser Arg Asp Asn Ser Lys Asn
                195                 200                 205

Thr Leu Tyr Leu Gln Met Asn Ser Leu Arg Ala Glu Asp Thr Ala Val
    210                 215                 220

Tyr Tyr Cys Ala Arg Asp Ala Gly Ile Ala Val Ala Gly Thr Gly Phe
225                 230                 235                 240

Asp Tyr Trp Gly Gln Gly Thr Leu Val Thr Val Ser Ser
                245                 250

<210> SEQ ID NO 6
<211> LENGTH: 117
<212> TYPE: PRT
<213> ORGANISM: Artificial Sequence
<220> FEATURE:
<223> OTHER INFORMATION: ESBA105 VH

<400> SEQUENCE: 6

Gln Val Gln Leu Val Gln Ser Gly Ala Glu Val Lys Lys Pro Gly Ala
1               5                   10                  15

Ser Val Lys Val Ser Cys Thr Ala Ser Gly Tyr Thr Phe Thr His Tyr
            20                  25                  30

Gly Met Asn Trp Val Arg Gln Ala Pro Gly Lys Gly Leu Glu Trp Met
        35                  40                  45

Gly Trp Ile Asn Thr Tyr Thr Gly Glu Pro Thr Tyr Ala Asp Lys Phe
    50                  55                  60

Lys Asp Arg Phe Thr Phe Ser Leu Glu Thr Ser Ala Ser Thr Val Tyr
65                  70                  75                  80

Met Glu Leu Thr Ser Leu Thr Ser Asp Asp Thr Ala Val Tyr Tyr Cys
                85                  90                  95

Ala Arg Glu Arg Gly Asp Ala Met Asp Tyr Trp Gly Gln Gly Thr Leu
            100                 105                 110

Val Thr Val Ser Ser
        115

<210> SEQ ID NO 7
<211> LENGTH: 121
<212> TYPE: PRT
<213> ORGANISM: Artificial Sequence
<220> FEATURE:
<223> OTHER INFORMATION: ESBA34max VH

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Ile Ser Arg Ser
            20                  25                  30

Tyr Trp Ile Cys Trp Val Arg Gln Ala Pro Gly Lys Gly Leu Glu Trp
        35                  40                  45

Val Ala Cys Ile Tyr Gly Asp Asn Asp Ile Thr Pro Leu Tyr Ala Asn
    50                  55                  60

Trp Ala Lys Gly Arg Phe Pro Val Ser Thr Asp Thr Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Leu Gly Tyr Ala Asp Tyr Ala Tyr Asp Leu Trp Gly
            100                 105                 110

Gln Gly Thr Leu Val Thr Val Ser Ser
```

<210> SEQ ID NO 8
<211> LENGTH: 122
<212> TYPE: PRT
<213> ORGANISM: Artificial Sequence
<220> FEATURE:
<223> OTHER INFORMATION: ESBA43max VH

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Gly Val Ile Ile Ser Ser Gly Ala Thr Tyr Tyr Ala Ser Trp Ala Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
        115                 120

<210> SEQ ID NO 9
<211> LENGTH: 122
<212> TYPE: PRT
<213> ORGANISM: Artificial Sequence
<220> FEATURE:
<223> OTHER INFORMATION: ESBA212 VH

<400> SEQUENCE: 9

Gln Val Gln Leu Val Gln Ser Gly Pro Glu Val Lys Lys Pro Gly Ala
1               5                   10                  15

Ser Val Lys Val Ser Cys Thr Ala Ser Gly Tyr Thr Phe Thr Glu Tyr
            20                  25                  30

Thr Met His Trp Val Arg Gln Ala Pro Gly Gln Gly Leu Glu Trp Met
        35                  40                  45

Gly Gly Val Asn Pro Tyr Asn Asp Asn Thr Ser Tyr Ile Arg Lys Leu
    50                  55                  60

Gln Gly Arg Val Thr Leu Thr Val Asp Arg Ser Ser Ser Thr Ala Tyr
65                  70                  75                  80

Met Glu Leu Thr Ser Leu Thr Ser Asp Asp Thr Ala Val Tyr Tyr Cys
                85                  90                  95

Ala Arg Tyr Gly Gly Leu Arg Pro Tyr Tyr Phe Pro Met Asp Phe Trp
            100                 105                 110

Gly Gln Gly Thr Leu Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: ESBA521 VH

<400> SEQUENCE: 10

-continued

```
Glu Val Gln Leu Val Glu Ser Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Ile Ala Val Ala Gly Thr Gly Phe Asp Tyr Trp
            100                 105                 110

Gly Gln Gly Thr Leu Val Thr Val Ser Ser
            115                 120
```

<210> SEQ ID NO 11
<211> LENGTH: 110
<212> TYPE: PRT
<213> ORGANISM: Artificial Sequence
<220> FEATURE:
<223> OTHER INFORMATION: ESBA105 VL

<400> SEQUENCE: 11

```
Met Ala Asp Ile Val Met Thr Gln Ser Pro Ser Ser Leu Ser Ala Ser
1               5                   10                  15

Val Gly Asp Arg Val Thr Leu Thr Cys Thr Ala Ser Gln Ser Val Ser
            20                  25                  30

Asn Asp Val Val Trp Tyr Gln Gln Arg Pro Gly Lys Ala Pro Lys Leu
            35                  40                  45

Leu Ile Tyr Ser Ala Phe Asn Arg Tyr Thr Gly Val Pro Ser Arg Phe
50                  55                  60

Ser Gly Arg Gly Tyr Gly Thr Asp Phe Thr Leu Thr Ile Ser Ser Leu
65                  70                  75                  80

Gln Pro Glu Asp Val Ala Val Tyr Tyr Cys Gln Gln Asp Tyr Asn Ser
                85                  90                  95

Pro Arg Thr Phe Gly Gln Gly Thr Lys Leu Glu Val Lys Arg
            100                 105                 110
```

<210> SEQ ID NO 12
<211> LENGTH: 111
<212> TYPE: PRT
<213> ORGANISM: Artificial Sequence
<220> FEATURE:
<223> OTHER INFORMATION: EP34max VL

<400> SEQUENCE: 12

```
Glu Ile Val Met Thr Gln Ser Pro Ser Thr Leu Ser Ala Ser Leu Gly
1               5                   10                  15

Asp Arg Val Ile Ile Thr Cys Gln Ser Ser Gln Ser Val Tyr Gly Asn
            20                  25                  30

Ile Trp Met Ala Trp Tyr Gln Gln Lys Ser Gly Lys Ala Pro Lys Leu
            35                  40                  45

Leu Ile Tyr Gln Ala Ser Lys Leu Ala Ser Gly Val Pro Ser Arg Phe
50                  55                  60

Ser Gly Ser Gly Ser Gly Ala Glu Phe Ser Leu Thr Ile Ser Ser Leu
65                  70                  75                  80
```

Gln Pro Asp Asp Phe Ala Thr Tyr Tyr Cys Gln Gly Asn Phe Asn Thr
            85                  90                  95

Gly Asp Arg Tyr Ala Phe Gly Gln Gly Thr Lys Leu Thr Val Leu
        100                 105                 110

<210> SEQ ID NO 13
<211> LENGTH: 111
<212> TYPE: PRT
<213> ORGANISM: Artificial Sequence
<220> FEATURE:
<223> OTHER INFORMATION: EP43max VL

<400> SEQUENCE: 13

Glu Ile Val Met Thr Gln Ser Pro Ser Thr Leu Ser Ala Ser Val Gly
1               5                   10                  15

Asp Arg Val Ile Ile Lys Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Phe Pro Ser Arg Phe Ser Gly
    50                  55                  60

Ser Gly Ser Gly Ala Glu Phe Thr Leu Thr Ile Ser Gly Leu Glu Pro
65                  70                  75                  80

Ala Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110

<210> SEQ ID NO 14
<211> LENGTH: 108
<212> TYPE: PRT
<213> ORGANISM: Artificial Sequence
<220> FEATURE:
<223> OTHER INFORMATION: ESBA212 VL

<400> SEQUENCE: 14

Ala Asp Ile Val Leu Thr Gln Ser Pro Ser Ser Leu Ser Ala Ser Val
1               5                   10                  15

Gly Asp Arg Val Thr Leu Thr Cys Arg Ala Ser Ser Ser Val Asn Tyr
            20                  25                  30

Met His Trp Tyr Gln Gln Arg Pro Gly Lys Pro Lys Ala Leu Ile
        35                  40                  45

Tyr Ala Thr Ser Asn Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Val Ala Val Tyr Tyr Cys Gln Gln Trp Arg Thr Asn Pro Pro
                85                  90                  95

Thr Phe Gly Gln Gly Thr Lys Leu Glu Val Lys Arg
            100                 105

<210> SEQ ID NO 15
<211> LENGTH: 111
<212> TYPE: PRT
<213> ORGANISM: Artificial Sequence
<220> FEATURE:
<223> OTHER INFORMATION: ESBA521 VL

<400> SEQUENCE: 15

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Asp Asn
                20                  25                  30

Tyr Val Ser Trp Tyr Gln Gln Leu Pro Gly Thr Ala Pro Gln Leu Leu
            35                  40                  45

Ile Tyr Asp Asn Thr Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
                100                 105                 110

<210> SEQ ID NO 16
<211> LENGTH: 29
<212> TYPE: PRT
<213> ORGANISM: Artificial Sequence
<220> FEATURE:
<223> OTHER INFORMATION: linker

<400> SEQUENCE: 16

Gly Gly Gly Gly Ser Gly Gly Gly Ser Cys Gly Gly Ser Gly
1               5                   10                  15

Gly Gly Cys Gly Gly Gly Ser Gly Gly Gly Ser
            20                  25

<210> SEQ ID NO 17
<211> LENGTH: 34
<212> TYPE: PRT
<213> ORGANISM: Artificial Sequence
<220> FEATURE:
<223> OTHER INFORMATION: linker

<400> SEQUENCE: 17

Gly Gly Gly Gly Ser Gly Gly Gly Ser Cys Gly Ala His Trp Gln
1               5                   10                  15

Phe Asn Ala Leu Thr Val Arg Cys Gly Gly Gly Ser Gly Gly Gly
            20                  25                  30

Gly Ser

<210> SEQ ID NO 18
<211> LENGTH: 72
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (12)..(61)
<223> OTHER INFORMATION: X can be any naturally occurring amino acid.
      at least three and up to 50 amino acids can be present

<400> SEQUENCE: 18

Gly Gly Gly Gly Ser Gly Gly Gly Ser Cys Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Cys Gly Gly
    50                  55                  60

Gly Gly Ser Gly Gly Gly Gly Ser
65                  70

<210> SEQ ID NO 19
<211> LENGTH: 83
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(15)
<223> OTHER INFORMATION: X can be any naturally occurring amino acid.
      at least three and up to 15 amino acids can be present
<220> FEATURE:
<221> NAME/KEY: MISC_FEATURE
<222> LOCATION: (17)..(66)
<223> OTHER INFORMATION: X can be any naturally occurring amino acid.
      at least three and up to 50 amino acids can be present
<220> FEATURE:
<221> NAME/KEY: MISC_FEATURE
<222> LOCATION: (69)..(83)
<223> OTHER INFORMATION: X can be any naturally occurring amino acid.
      at least three and up to 15 amino acids can be present

<400> SEQUENCE: 19

Xaa Xaa Xaa Xaa Xaa Xaa Xaa Xaa Xaa Xaa Xaa Xaa Xaa Xaa Cys
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Cys Gly Xaa Xaa Xaa Xaa Xaa Xaa Xaa Xaa Xaa Xaa Xaa
65                  70                  75                  80

Xaa Xaa Xaa

<210> SEQ ID NO 20
<211> LENGTH: 232
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (26)..(75)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least one and up to 50 amino acids can be present

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa

```
                50                  55                  60
Xaa Xaa Xaa Xaa Xaa Xaa Xaa Xaa Xaa Xaa Trp Val Arg Gln Ala
 65                  70                  75                  80

Pro Gly Lys Gly Leu Glu Trp Val Ser Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
                115                 120                 125

Xaa Xaa Xaa Xaa Xaa Xaa Xaa Xaa Xaa Xaa Xaa Arg Phe Thr Ile Ser
            130                 135                 140

Arg Asp Asn Ser Lys Asn Thr Leu Tyr Leu Gln Met Asn Ser Leu Arg
145                 150                 155                 160

Ala Glu Asp Thr Ala Val Tyr Tyr Cys Ala Lys Xaa Xaa Xaa Xaa
                165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa Xaa Xaa Xaa Xaa Xaa Xaa Xaa
                195                 200                 205

Xaa Xaa Xaa Xaa Xaa Xaa Xaa Xaa Xaa Xaa Xaa Xaa Trp Gly Gln
                210                 215                 220

Gly Thr Leu Val Thr Val Ser Ser
225                 230

<210> SEQ ID NO 21
<211> LENGTH: 231
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present

<400> SEQUENCE: 21

Glu Ile Val Met Thr Gln Ser Pro Ser Thr Leu Ser Ala Ser Val Gly
 1               5                  10                  15

Asp Arg Val Ile Ile Thr Cys Xaa Xaa Xaa Xaa Xaa Xaa Xaa Xaa
                 20                  25                  30

Xaa Xaa Xaa Xaa Xaa Xaa Xaa Xaa Xaa Xaa Xaa Xaa Xaa Xaa Xaa
                 35                  40                  45

Xaa Xaa Xaa Xaa Xaa Xaa Xaa Xaa Xaa Xaa Xaa Xaa Xaa Xaa Xaa
                 50                  55                  60

Xaa Xaa Xaa Xaa Xaa Xaa Xaa Xaa Trp Tyr Gln Gln Lys Pro Gly
 65                  70                  75                  80

Lys Ala Pro Lys Leu Leu Ile Tyr Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa
                100                 105                 110
```

```
Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
        130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Phe Gly Gln Gly
        210                 215                 220

Thr Lys Leu Thr Val Leu Gly
225                 230

<210> SEQ ID NO 22
<211> LENGTH: 483
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(472)
<223> OTHER INFORMATION: X can be any naturally occurring amino acid.
      at least one and up to 50 amino acids can be present

<400> SEQUENCE: 22

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Trp Tyr Gln Gln Lys Pro Gly
65                  70                  75                  80
```

```
Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Gly Val Pro Ser Arg Phe
            130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Phe Gly Gln Gly
            210                 215                 220

Thr Lys Leu Thr Val Leu Gly Gly Gly Gly Ser Gly Gly Gly Gly
225                 230                 235                 240

Ser Gly Gly Gly Gly Ser Gly Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Ala Ala Ser Xaa Xaa Xaa Xaa Xaa Xaa Xaa Xaa Xaa Xaa Xaa
                275                 280                 285

Xaa Xaa Xaa Xaa Xaa Xaa Xaa Xaa Xaa Xaa Xaa Xaa Xaa Xaa Xaa
            290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Ser Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Arg Phe Thr Ile Ser Arg Asp Asn Ser Lys
385                 390                 395                 400

Asn Thr Leu Tyr Leu Gln Met Asn Ser Leu Arg Ala Glu Asp Thr Ala
                405                 410                 415

Val Tyr Tyr Cys Ala Lys Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 23
<211> LENGTH: 232
```

```
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (26)..(75)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least one and up to 50 amino acids can be present

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Thr Ala Ser Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Arg Phe Thr Ile Ser
    130                 135                 140

Arg Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 24
<211> LENGTH: 231
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
```

```
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present

<400> SEQUENCE: 24

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Gly Val Pro Ser Arg Phe
    130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Phe Gly Gln Gly
    210                 215                 220

Thr Lys Leu Thr Val Leu Gly
225                 230

<210> SEQ ID NO 25
<211> LENGTH: 483
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
```

-continued

```
<221> NAME/KEY: MISC_FEATURE
<222> LOCATION: (277)..(326)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(472)
<223> OTHER INFORMATION: X can be any naturally occurring amino acid.
      at least one and up to 50 amino acids can be present

<400> SEQUENCE: 25

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly
225                 230                 235                 240

Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
            260                 265                 270

Cys Thr Ala Ser Xaa Xaa Xaa Xaa Xaa Xaa Xaa Xaa Xaa Xaa
            275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335
```

```
Glu Trp Val Gly Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa
    370                 375                 380

Xaa Xaa Xaa Xaa Xaa Xaa Arg Phe Thr Ile Ser Arg Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa
    450                 455                 460

Xaa Xaa Xaa Xaa Xaa Xaa Xaa Trp Gly Gln Gly Thr Leu Val Thr
465                 470                 475                 480

Val Ser Ser

<210> SEQ ID NO 26
<211> LENGTH: 232
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (26)..(75)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (90)..(139)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (172)..(221)
<223> OTHER INFORMATION: X can be any naturally occurring amino acid.
      at least one and up to 50 amino acids can be present

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Thr Val Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Gly Xaa Xaa Xaa Xaa Xaa Xaa
            85                  90                  95

Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Arg Phe Thr Ile Ser
    130                 135                 140
```

```
Lys Asp Thr Ser Lys Asn Thr Val Tyr Leu Gln Met Asn Ser Leu Arg
145                 150                 155                 160

Ala Glu Asp Thr Ala Val Tyr Tyr Cys Ala Arg Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Xaa Trp Gly Gln
210                 215                 220

Gly Thr Leu Val Thr Val Ser Ser
225                 230

<210> SEQ ID NO 27
<211> LENGTH: 483
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (24)..(73)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (89)..(138)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (171)..(220)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (277)..(326)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (341)..(390)
<223> OTHER INFORMATION: X can be any naturally occurring amino acid.
      at least one and up to 50 amino acids can be present
<220> FEATURE:
<221> NAME/KEY: MISC_FEATURE
<222> LOCATION: (423)..(472)
<223> OTHER INFORMATION: X can be any naturally occurring amino acid.
      at least one and up to 50 amino acids can be present

<400> SEQUENCE: 27

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110
```

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Gly Val Pro Ser Arg Phe
130                 135                 140

Ser Gly Ser Gly Ser Gly Thr Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa
                165                 170                 175

Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
        210                 215                 220

Thr Lys Leu Thr Val Leu Gly Gly Gly Gly Ser Gly Gly Gly
225                 230                 235                 240

Ser Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

Cys Thr Val Ser Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Gly Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa
        370                 375                 380

Xaa Xaa Xaa Xaa Xaa Xaa Arg Phe Thr Ile Ser Lys Asp Thr Ser Lys
385                 390                 395                 400

Asn Thr Val Tyr Leu Gln Met Asn Ser Leu Arg Ala Glu Asp Thr Ala
                405                 410                 415

Val Tyr Tyr Cys Ala Arg Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Trp Gly Gln Gly Thr Leu Val Thr
465                 470                 475                 480

Val Ser Ser

<210> SEQ ID NO 28
<211> LENGTH: 5
<212> TYPE: PRT
<213> ORGANISM: Artificial Sequence
<220> FEATURE:
<223> OTHER INFORMATION: penetration enhancer

<400> SEQUENCE: 28

Pro Leu Gly Pro Arg
1               5

<210> SEQ ID NO 29
<211> LENGTH: 5
<212> TYPE: PRT
<213> ORGANISM: Artificial Sequence
<220> FEATURE:
<223> OTHER INFORMATION: penetration enhancer

<400> SEQUENCE: 29

Pro Leu Gly Pro Lys
1               5

<210> SEQ ID NO 30
<211> LENGTH: 5
<212> TYPE: PRT
<213> ORGANISM: Artificial Sequence
<220> FEATURE:
<223> OTHER INFORMATION: penetration enhancer

<400> SEQUENCE: 30

Pro Leu Gly Pro Glu
1               5

<210> SEQ ID NO 31
<211> LENGTH: 5
<212> TYPE: PRT
<213> ORGANISM: Artificial Sequence
<220> FEATURE:
<223> OTHER INFORMATION: penetration enhancer

<400> SEQUENCE: 31

Pro Leu Gly Pro Asp
1               5

<210> SEQ ID NO 32
<211> LENGTH: 4
<212> TYPE: PRT
<213> ORGANISM: Artificial Sequence
<220> FEATURE:
<223> OTHER INFORMATION: penetratin enhancer

<400> SEQUENCE: 32

Pro Leu Gly Pro
1

<210> SEQ ID NO 33
<211> LENGTH: 252
<212> TYPE: PRT
<213> ORGANISM: Artificial Sequence
<220> FEATURE:
<223> OTHER INFORMATION: ESBA903 scFv

<400> SEQUENCE: 33

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

```
Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly Gly
            100                 105                 110

Gly Gly Gly Gly Ser Gly Gly Gly Gly Ser Gly Gly Gly Gly Ser Ser
            115                 120                 125

Gly Gly Gly Ser Glu Val Gln Leu Val Glu Ser Gly Gly Gly Leu Val
130                 135                 140

Gln Pro Gly Gly Ser Leu Arg Leu Ser Cys Thr Ala Ser Gly Phe Ser
145                 150                 155                 160

Leu Thr Asp Tyr Tyr Met Thr Trp Val Arg Gln Ala Pro Gly Lys
                165                 170                 175

Gly Leu Glu Trp Val Gly Phe Ile Asp Pro Asp Asp Pro Tyr Tyr
            180                 185                 190

Ala Thr Trp Ala Lys Gly Arg Phe Thr Ile Ser Arg Asp Thr Ser Lys
            195                 200                 205

Asn Thr Val Tyr Leu Gln Met Asn Ser Leu Arg Ala Glu Asp Thr Ala
            210                 215                 220

Val Tyr Tyr Cys Ala Gly Gly Asp His Asn Ser Gly Trp Gly Leu Asp
225                 230                 235                 240

Ile Trp Gly Gln Gly Thr Leu Val Thr Val Ser Ser
                245                 250

<210> SEQ ID NO 34
<211> LENGTH: 111
<212> TYPE: PRT
<213> ORGANISM: Artificial Sequence
<220> FEATURE:
<223> OTHER INFORMATION: ESBA903 VL

<400> SEQUENCE: 34

Glu Ile Val Met Thr Gln Ser Pro Ser Thr Leu Ser Ala Ser Val Gly
1               5                   10                  15

Asp Arg Val Ile Ile Thr Cys Gln Ala Ser Glu Ile Ile His Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Asn Val Tyr Leu Ala Ser Thr
                85                  90                  95

Asn Gly Ala Asn Phe Gly Gln Gly Thr Lys Leu Thr Val Leu Gly
            100                 105                 110

<210> SEQ ID NO 35
<211> LENGTH: 120
<212> TYPE: PRT
<213> ORGANISM: Artificial Sequence
<220> FEATURE:
<223> OTHER INFORMATION: ESBA903 VH

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Thr Asp Tyr
            20                  25                  30
```

```
Tyr Tyr Met Thr Trp Val Arg Gln Ala Pro Gly Lys Gly Leu Glu Trp
            35                  40                  45

Val Gly Phe Ile Asp Pro Asp Asp Pro Tyr Tyr Ala Thr Trp Ala
    50                  55                  60

Lys Gly Arg Phe Thr Ile Ser Arg Asp Thr Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Gly Gly Asp His Asn Ser Gly Trp Gly Leu Asp Ile Trp Gly Gln
                100                 105                 110

Gly Thr Leu Val Thr Val Ser Ser
            115                 120

<210> SEQ ID NO 36
<211> LENGTH: 20
<212> TYPE: PRT
<213> ORGANISM: Artificial Sequence
<220> FEATURE:
<223> OTHER INFORMATION: linker

<400> SEQUENCE: 36

Gly Gly Gly Gly Ser Gly Gly Gly Ser Gly Gly Gly Ser Gly
1               5                   10                  15

Gly Gly Gly Ser
            20

<210> SEQ ID NO 37
<211> LENGTH: 20
<212> TYPE: PRT
<213> ORGANISM: Artificial Sequence
<220> FEATURE:
<223> OTHER INFORMATION: linker

<400> SEQUENCE: 37

Gly Gly Gly Gly Ser Gly Gly Gly Gly Ser Gly Gly Gly Gly Ser Ser
1               5                   10                  15

Gly Gly Gly Ser
            20
```

US 8,697,074 B2

METHODS AND COMPOSITIONS FOR ENHANCED DELIVERY OF MACROMOLECULES

RELATED APPLICATIONS

The present application is a 371 application, which claims priority from PCT/CH2009/000248, filed Jul. 10, 2009; which claims priority to U.S. Provisional Application No. 61/079,586, filed Jul. 10, 2008, the contents of which are hereby incorporated by reference.

FIELD OF INVENTION

The present disclosure relates to compositions and methods that facilitate delivery of molecules across biological membranes, particularly to delivery of antigen-binding polypeptides across the blood-brain barrier into the central nervous system (CNS).

BACKGROUND OF THE INVENTION

According to a 2006 World Health Organization report, over 1 billion people worldwide are afflicted with a neurological disorder, and such disorders result in nearly 6.8 million deaths annually. Therapeutic antigen binding peptides, such as antibodies, could be used for treatment of many, if not the majority, of these neurological disorders. However, treatment of neurological disorders using such therapeutic antigen-binding peptides is frequently hampered by difficulties associated with delivering drugs across the blood-brain barrier (BBB).

Although compounds that enhance the delivery of molecules across epithelial cell layers have been discovered, they have generally been shown to be only effective at enhancing the delivery of small molecules. For example, the peptide 4-phenylazobenzyl oxycarbonyl-Pro-Leu-Gly-Pro has been shown to enhance the transport of small molecules across epithelial cell layers, whereas no penetration enhancing effect was demonstrated for macromolecules of 10 kDa and larger (see U.S. Pat. No. 5,534,496; Yen et al. 1995, J Control Release, 36:25-37). Despite being heavily investigated, there is presently no convenient and efficient method for the delivery of therapeutic antigen-binding polypeptides into the CNS.

There is therefore a continuing need in the art for compositions and methods that enhance the specific delivery of therapeutic antigen-binding polypeptides across epithelial layers, in particular to the CNS for the treatment of CNS disorders.

SUMMARY OF THE INVENTION

The present invention is based, at least in part, on the surprising discovery that penetration enhancers (e.g., Pz-peptide or FMOC-peptide) are capable of enhancing the specific delivery of large macromolecules (i.e., greater than 10 kDa) such as antigen-binding polypeptides (e.g. scFv) to the CNS, particularly when administered to nasal mucosa. Accordingly, the invention provides compositions and methods that enhance the delivery of large macromolecules (i.e., greater than 10 kDa), such as antigen-binding polypeptides (e.g., scFv), across epithelial layers. Such methods and compositions are particularly advantageous in that they enable the convenient, efficient, and selective delivery of an antigen-binding polypeptide (e.g., scFv) to the CNS, via intranasal administration, for the treatment of neurological disorders.

In one aspect, the invention provides compositions comprising one or more antigen-binding polypeptides, such as an immunobinder (e.g., scFv), and one or more penetration enhancers (e.g., Pz-peptide or FMOC—peptide). In a particular embodiment, an antigen-binding polypeptide is covalently linked to a penetration enhancer.

In certain embodiments, the antigen-binding polypeptide specifically binds to a target antigen selected from the group consisting of TNF-alpha, amyloid beta, amyloid beta-derived diffusible ligand receptor, monoamine oxidase-B, L-3,4-dihydroxyphenylalanine decarboxylase, acetyl-coA carboxylase, N-methyl-D-aspartate receptor (also known as GRIN1), GRINA, GRIN2A, GRIN2B, GRIN2C, GRIN2D, GRIN3A, GRIN3B, histamine H1 Receptor, muscarinic receptor (also known as CHRM1), CHRM2, CHRM3, CHRM4, hypocretin receptor 1, hypocretin receptor 2,5-hydroxytryptamine (also known as HTR1A), dopamine receptor (also known as DRD1), DRD2, DRD3, DRD4, DRD5, adrenergic beta 1 receptor, norepinephrin transporter (NET), and dopamine D2 receptor, in particular to TNFalpha.

In other embodiments, the antigen-binding polypeptide is a scFv comprising an amino acid sequence with at least 80% preferably 85%, 90%, 95%, or 99% identity or similarity to one or more amino acid sequences set forth in Tables 5, 6, and 7 herein.

In other embodiments, the penetration enhancer facilitates the selective intranasal delivery of the antigen-binding polypeptide to the central nervous system.

The compositions of the invention are particularly useful as medicaments (or for the manufacture of medicaments), in particular, for the treatment, prevention or delay of progression of a neurological disorder, including, without limitation, migraine, depression, Alzheimer's disease, Parkinson's disease, schizophrenia, epilepsy, stroke, meningitis, amyotrophic lateral sclerosis, insomnia, meningitis, memory impairment, multiple sclerosis, narcolepsy, stroke, traumatic brain injury, and stress.

In another aspect, the invention provides a kit comprising one or more antigen-binding polypeptides (e.g., scFv), one or more penetration enhancers (e.g., Pz-peptide or FMOC-peptide), and instructions for use.

DESCRIPTION OF THE DRAWINGS

The features and advantages of the present disclosure will be better understood when reading the following detailed description, taken together with the following drawings in which.

DETAILED DESCRIPTION

Definitions

Figure 1A:
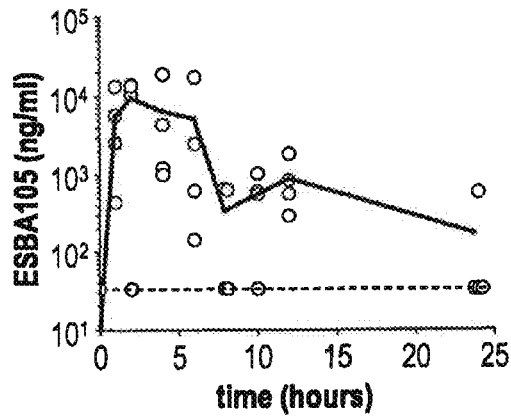
FIG. 1 depicts time course experiments that track ESBA105 concentrations in the (A) olfactory bulb, (B) cerebrum, (C) cerebellum, (D) brainstem, and (E) serum following intranasal administration of 400 µg scFv.
Figure 1B:
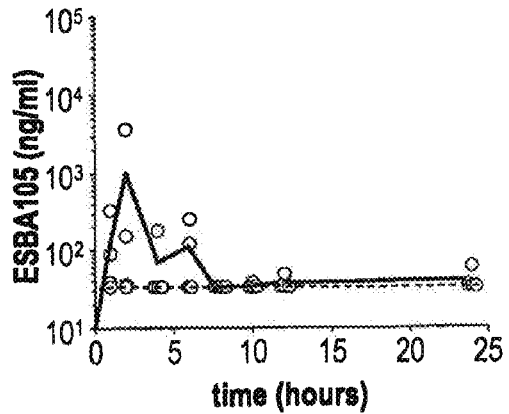
Figure 1C:
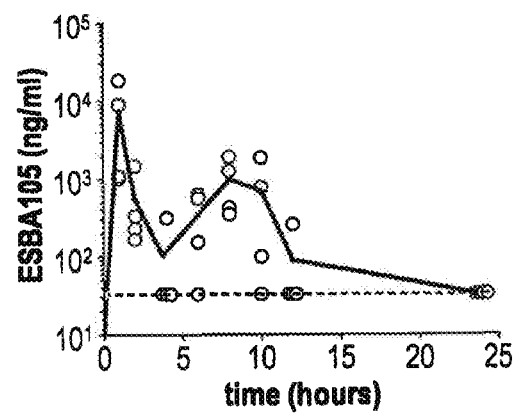
Figure 1D:
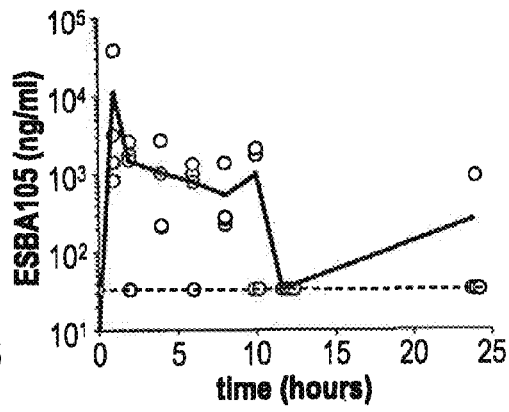
Figure 1E:
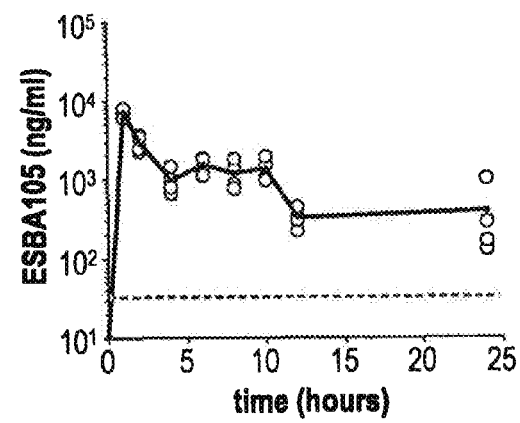
Figure 2A:
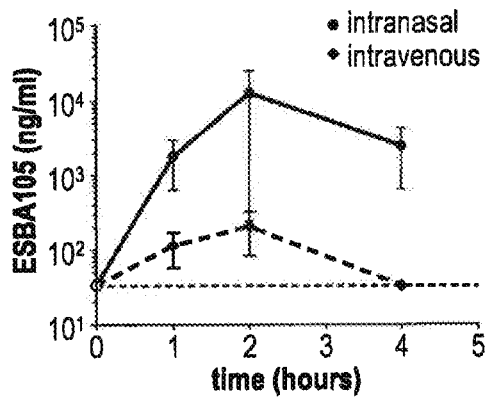
FIG. 2 compares ESBA105 concentrations in the (A) olfactory bulb, (B) cerebrum, (C) cerebellum, (D) brainstem, and (E) serum following either intranasal (400 µg/mL) or intravenous (40 µg/mL) administration of ESBA105, as well as in (F) serum following either intranasal or intravenous administration of ESBA105 at equal concentrations of 400 µg/mL.
Figure 2B:
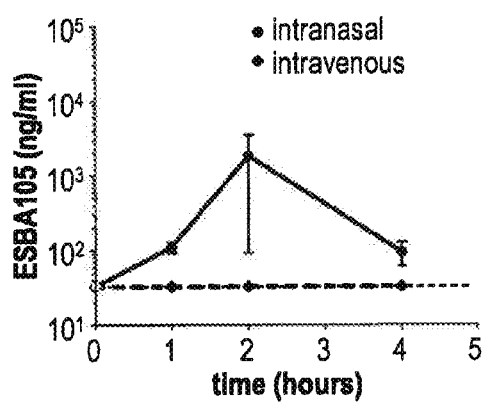
Figure 2C:
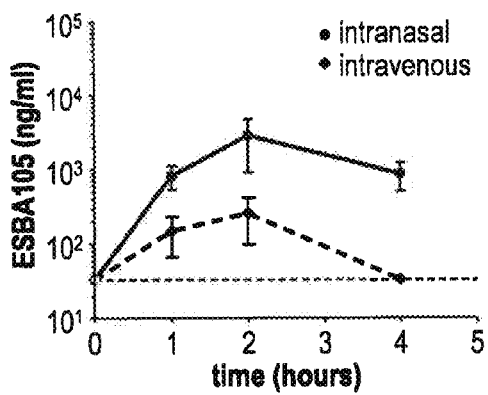
Figure 2D:
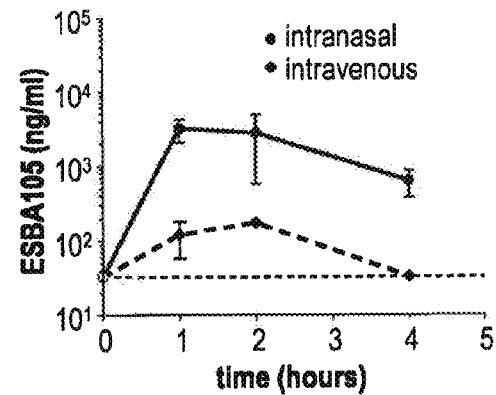
Figure 2E:
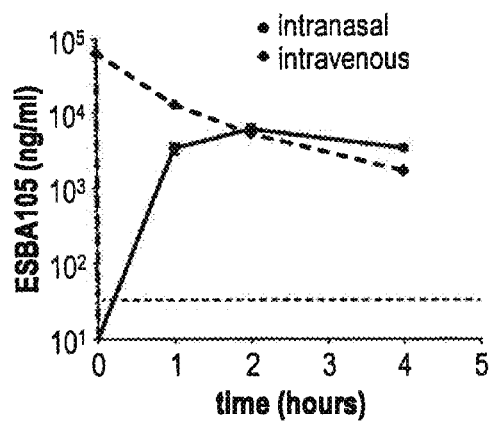
Figure 2F:
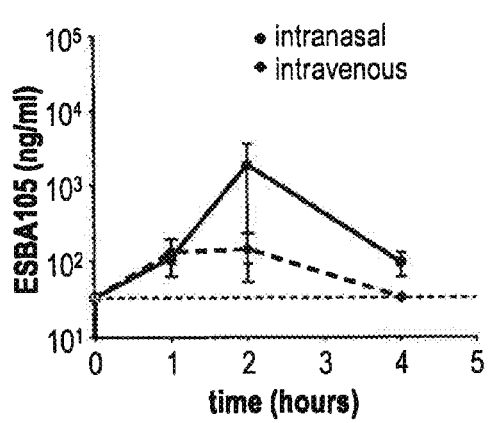
Figure 3A:
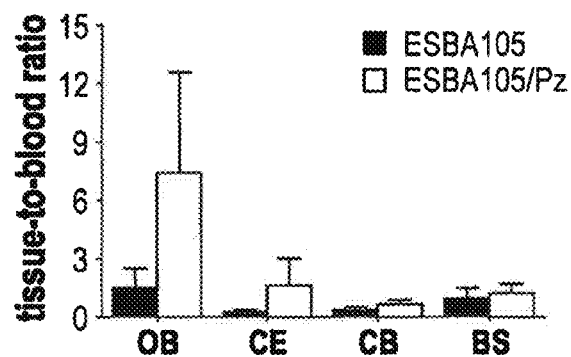
FIG. 3 shows (A) $C_{max}$ (mean values±SEM, n=4) and (B) exposure (AUC) brain tissue-to-blood concentration ratios of ESBA105 in different brain regions following intranasal administration with or without Pz peptide.
Figure 3B:
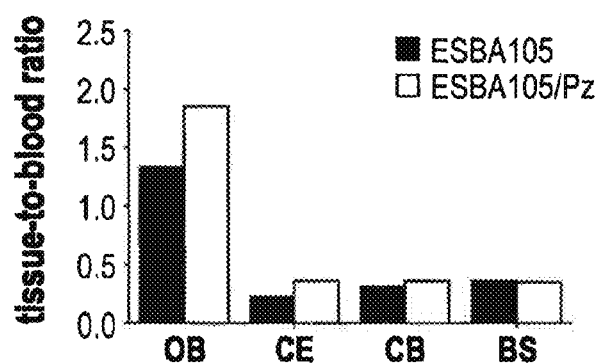
Figure 4:
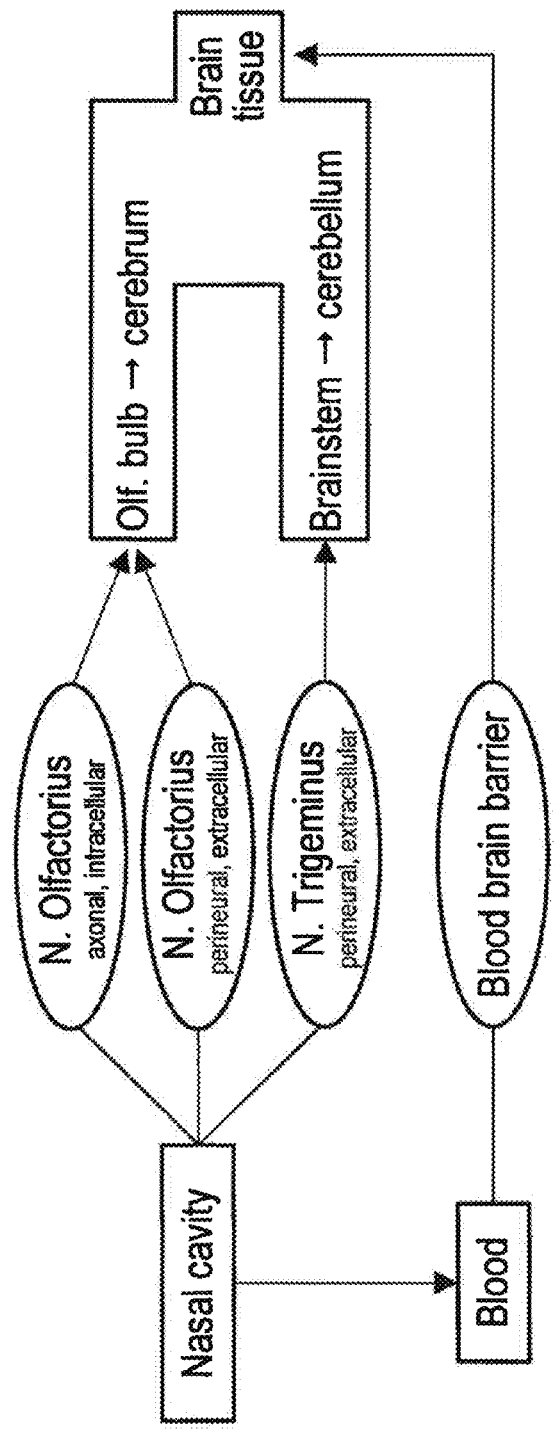
FIG. 4 depicts migration routes of ESBA105 from the nasal cavity to the CNS following intranasal delivery. From the nasal cavity, an administered compound may migrate into the blood and pass the blood brain barrier to finally penetrate into the brain tissue (lower route). Alternatively, the compound may migrate via the *N. olfactorius* axonally (i.e. intracellular) or perineurnally (i.e. extracellular) into the olfactory bulb and subsequently into the cerebrum. The compound may also migrate via the *N. trigeminus* (perineurally, i.e. extracellularly) into the brain stem and then into the cerebellum.

The term "penetration enhancer" encompasses any composition that enhances the passage of a drug across a physical barrier such as a tissue barrier (e.g. an epithelium). Suitable penetration enhancers include, without limitation, the peptides Pro-Leu-Gly-Pro-Arg [SEQ ID NO: 28], Pro-Leu-Gly-Pro-Lys [SEQ ID NO: 29], Pro-Leu-Gly-Pro-Glu [SEQ ID NO: 30], Pro-Leu-Gly-Pro-Asp [SEQ ID NO: 31], Pro-Leu-Gly-Pro [SEQ ID NO: 32], Pro-Leu-Gly and Pro-Leu, N-terminally linked to a protective group such as 4-phenylazobenzyloxycarbonyl (Pz), N-methyl, t-butyloxcarbonyl (t-Boc), fluoroenylmethyloxycarbonyl (FMOC), and carbobenzoxy (CBZ) (see e.g. U.S. Pat. No. 5,534,496, which is hereby incorporated by reference).

The term "Pz-peptide" refers to Pro-Leu-Gly-Pro-Arg [SEQ ID NO: 28], N-terminally linked to a Pz group (see e.g. U.S. Pat. No. 5,534,496, which is hereby incorporated by reference).

The term "FMOC-peptide" refers to Pro-Leu-Gly-Pro-Arg [SEQ ID NO: 28], N-terminally linked to a FMOC group (see e.g. U.S. Pat. No. 5,534,496, which is hereby incorporated by reference).

The term "selective intranasal delivery" refers to the intranasal application of a molecule (e.g., an antigen-binding polypeptide) to a patient under conditions that result in higher concentrations of the molecule in the CNS than in the serum of a patient.

The term "antigen-binding polypeptide" refers to polypeptides that are at least 10 kDa in size, and includes immunobinders, monoclonal antibodies (including full length monoclonal antibodies), polyclonal antibodies, multispecific antibodies (e.g., bispecific antibodies), chimeric antibodies, CDR-grafted antibodies, humanized antibodies, human antibodies, single chain antibodies (scFvs), and antibody fragments, as well as antigen-binding polypeptides based on alternative scaffolds known in the art such as, but not limited to, CTLA-4, tendamistat, fibronectin (FN3), neocarzinostatin, CBM4-2, lipocalins, T-cell receptor, Protein A domain (protein Z), Im9, designed ankyrin-repeat proteins (DARPins), designed TPR proteins, zinc finger, pVIII, avian pancreatic polypeptide, GCN4, WW domain, Src homology domain 3 (SH3), Src homology domain 2 (SH2), PDZ domains, TEM-1 β-lactamase, GFP, thioredoxin, staphylococcal nuclease, PHD-finger, $C_{L-2}$, BPT1 APPI, HPSTI, ecotin, LACI-D1, LDTI, MTI-II, scorpion toxins, insect defensin A peptide, EETI-II, Min-23, CBD, PBP, cytochrome $b_{562}$, Ldl receptor domain A, γ-crystallin, ubiquitin, transferrin, and C-type lectin-like domain (see e.g. Binz 2005, Curr Opin Biotechnol. Vol. 16 p. 459-69).

The term "immunobinder" refers to a molecule that contains all or a part of the antigen binding site of an antibody, e.g., all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, Fundamental Immunology (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a single domain antibody such as a Dab fragment (Ward et al., (1989) *Nature* 341:544-546)), which consists of a $V_H$ or $V_L$ domain, a Camelid (see e.g. Hamers-Casterman, et al., Nature 363:446-448 (1993) and Dumoulin, et al., Protein Science 11:500-515 (2002)) or a Shark antibody (e.g., shark Ig-NARs Nanobodies®); and (vii) a nanobody, a heavy chain variable region containing a single variable domain and two constant domains.

The term "antibody" as used herein is a synonym for "immunoglobulin." Antibodies according to the present invention may be whole immunoglobulins or fragments thereof, comprising at least one variable domain of an immunoglobulin, such as single variable domains, Fv (Skerra A. and Pluckthun, A. (1988) Science 240:1038-41), scFv (Bird, R. E. et al. (1988) Science 242:423-26; Huston, J. S. et al. (1988) Proc. Natl. Acad. Sci. USA 85:5879-83), Fab, (Fab')$_2$ or other fragments well known to a person skilled in the art.

The term "single chain antibody" or "scFv" refers to a molecule comprising an antibody heavy chain variable region ($V_H$) and an antibody light chain variable region ($V_L$) connected by a linker. Such scFv molecules may have the general structures: $NH_2$-$V_L$-linker-$V_H$-COOH or $NH_2$-$V_H$-linker-$V_L$-COOH.

The term "antibody framework" as used herein refers to the part of the variable domain, either VL or VH, which serves as a scaffold for the antigen binding loops of this variable domain (Kabat, E. A. et al., (1991) Sequences of proteins of immunological interest. NIH Publication 91-3242). Examples of suitable frameworks are disclosed in PCT/CH2009/000219 and PCT/CH2009/000222, which are hereby incorporated by reference herein.

The term "linker" refers to a linear amino acid sequence linking two domains. Linkers of the invention may be genetically and/or chemically fused to a domain. In certain embodiments, linkers contain a loop formed via a disulfide bridge formed between two cysteines present in the linker. The general structure of such a linker is given in SEQ ID Nos. 18 and 19; SEQ ID Nos. 16 and 17 are exemplary embodiments of said linkers. A further suitable state of the art linker consists of repeated GGGGS amino acid sequences or variants thereof. In a preferred embodiment of the present invention a (GGGGS)$_4$ linker (SEQ ID No: 36) or its derivative (e.g. is used SEQ ID No: 37) is used, but variants of 1-3 repeats are also possible (Holliger et al. (1993), Proc. Natl. Acad. Sci. USA 90:6444-6448). Other linkers that may be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. Immunother. 50:51-59.

The term "modified" or "modifying," with respect to the amino acid sequence of a polypeptide, refers to both the addition of amino acids into the polypeptide sequence or the substitution of existing amino acids in the polypeptide sequence. Amino acids suitable for modifying a polypeptide include all known natural amino acids, unnatural amino acids, and functionalized derivatives thereof (see. e.g., U.S. Pat. Nos. 7,045,337 and 7,083,970, which are hereby incorporate by reference in their entireties). In certain embodiments, the term refers to the deletion of amino acids from the polypeptide sequence.

A "target antigen" is a molecule (e.g., a soluble protein or a membrane-bound protein, having one or more membrane-spanning domains, a polypeptide, a peptide or a carbohydrate) containing an antigenic determinant to which an antibody specifically binds.

The term "neurological disorder" includes diseases and disorders that may affect the central nervous system (i.e. the brain and spinal cord).

The term CNS disorder refers to a disorder that is manifested in the CNS. By way of example, this may be a brain tumor or a neurological disorder.

The term "effective amount" is defined as an amount of a therapeutic (e.g. an antigen-binding polypeptide) sufficient to partially, or completely prevent or arrest a disease or disorder (e.g., a neurological disorder) in a patient. The effective amount will depend upon the severity of the disease or disorder and a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The term "patient" includes human and other mammalian subjects that receive either prophylactic or therapeutic treatment.

The terms "specific binding," "selective binding," "selectively binds," and "specifically binds," refer to antibody binding to an epitope on a predetermined antigen. Typically, the antibody binds with an affinity ($K_D$) of approximately less than about $10^{-7}$ M, such as approximately less than about $10^{-8}$ M, $10^{-9}$ M or $10^{-10}$ M.

As used herein, "identity" refers to the sequence matching between two polypeptides, molecules or between two nucleic acids. When a position in both of the two compared sequences is occupied by the same base or amino acid monomer subunit (for instance, if a position in each of the two DNA molecules is occupied by adenine, or a position in each of two polypeptides is occupied by a lysine), then the respective molecules are identical at that position. The "percentage identity" between two sequences is a function of the number of matching positions shared by the two sequences divided by the number of positions compared ×100. For instance, if 6 of 10 of the positions in two sequences are matched, then the two sequences have 60% identity. By way of example, the DNA sequences CTGACT and CAGGTT share 50% identity (3 of the 6 total positions are matched). Generally, a comparison is made when two sequences are aligned to give maximum identity. Such alignment may be provided using, for instance, the method of Needleman et al. (1970) *J. Mol. Biol.* 48: 443-453, implemented conveniently by computer programs such as the Align program (DNAstar, Inc.). The percent identity between two amino acid sequences may also be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J. Mol. Biol.* 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

"Similar" sequences are those which, when aligned, share identical and similar amino acid residues, where similar residues are conservative substitutions for corresponding amino acid residues in an aligned reference sequence. In this regard, a "conservative substitution" of a residue in a reference sequence is a substitution by a residue that is physically or functionally similar to the corresponding reference residue, e.g., that has a similar size, shape, electric charge, chemical properties, including the ability to form covalent or hydrogen bonds, or the like. Thus, a "conservative substitution modified" sequence is one that differs from a reference sequence or a wild-type sequence in that one or more conservative substitutions are present. The "percentage similarity" between two sequences is a function of the number of positions that contain matching residues or conservative substitutions shared by the two sequences divided by the number of positions compared ×100. For instance, if 6 of 10 of the positions in two sequences are matched and 2 of 10 positions contain conservative substitutions, then the two sequences have 80% positive similarity.

As used herein, the term "conservative sequence modifications" is intended to refer to amino acid modifications that do not negatively affect or alter the binding characteristics of the antibody containing the amino acid sequence. Such conservative sequence modifications include nucleotide and amino acid substitutions, additions and deletions. For example, modifications may be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-VEGF antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10): 879-884 (1999); and Burks et al. *Proc. Natl. Acad. Sci. USA* 94:412-417 (1997))

Unless otherwise defined, all technical and scientific terms used herein have the same meaning as commonly understood by one of ordinary skill in the art to which this invention belongs. Although methods and materials similar or equivalent to those described herein may be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments may be combined at will.

Improved Antigen-Binding Polypeptide Compositions

In one aspect, the invention provides compositions for enhancing the delivery of therapeutic polypeptides, such as antigen-binding polypeptides (e.g., scFv) across tissue barriers, more particularly across the nasal mucosa into the CNS. Such compositions generally comprise an antigen-binding polypeptide and a penetration enhancer. These compositions are particularly advantageous in that they are capable of selective intranasal delivery of the antigen-binding polypeptide to the central nervous system. Today, biologics are typically systemically administered requiring thus a higher dose of the drug and/or subjecting the organism in need thereof to the drug; alternatively, the biologic may be administered via a cranial cannula. Therefore, the present invention significantly improves life quality of a subject in need of the antigen-binding polypeptide.

Any antigen-binding polypeptide is suitable for use in the methods of the invention. In certain embodiments, the antigen-binding polypeptide is an immunobinder, such as an scFv. Such scFv preferably comprise highly stable and soluble framework regions such as those set forth in WO09/000,098, the contents of which are incorporated herein by reference. In a particularly preferred embodiment, the scFv comprises an amino acid sequence with at least 80% similarity (e.g., 85%, 90%, 95%, or 99%) to one or more amino acid sequences set forth in Tables 5, 6, and 7. Most preferably, the scFv comprises an amino acid sequence with at least 80% identity, preferably 85%, 90%, 95%, or 99% identity, to one or more amino acid sequences set forth in Tables 5, 6, and 7.

In a preferred embodiment, said scFv comprises a framework sequence having at least at least 80% similarity (e.g., 85%, 90%, 95%, or 99%), more preferably at least 80% identity, even more preferably 85%, 90%, 95%, or 99% identity, to SEQ ID No: 20, SEQ ID No: 21, SEQ ID No: 22, SEQ ID No: 23, SEQ ID No: 24, SEQ ID No: 25, SEQ ID No: 26, or SEQ ID No: 27.

In another embodiment, said scFv comprises a VH domain comprising an amino acid sequence with at least 80% similarity (e.g., 85%, 90%, 95%, or 99%), more preferably at least 80% identity, even more preferably 85%, 90%, 95%, or 99% identity, to SEQ ID No: 6, SEQ ID No: 7, SEQ ID No: 8, SEQ ID No: 9, SEQ ID No: 10, or SEQ ID No:35. Additionally or alternatively, said scFv comprises a VL domain comprising an amino acid sequence with at least 80% similarity (e.g., 85%, 90%, 95%, or 99%), more preferably at least 80% identity, even more preferably 85%, 90%, 95%, or 99% identity, to SEQ ID No: 11, SEQ ID No: 12, SEQ ID No: 13, SEQ ID No: 14, SEQ ID No: 15, or SEQ ID No:34. In one embodiment, said VH and/or VL are linked by a linker to yield a molecule having the general structure NH2-VH-linker-VL-COOH or NH2-VL-linker-VH-COOH. Said linker molecule may e.g. be selected by the group consisting of SEQ ID NO: 16, SEQ ID NO: 17, SEQ ID NO: 18, SEQ ID NO: 19, SEQ ID NO:36 and SEQ ID NO: 37 or is a sequence having at least 80% similarity thereto.

In a preferred embodiment, the scFv comprises an amino acid sequence with at least 80% similarity (e.g., 85%, 90%, 95%, or 99%), more preferably at least 80% identity, even more preferably 85%, 90%, 95%, or 99% identity, to SEQ ID No: 1, SEQ ID No: 2, SEQ ID No: 3, SEQ ID No: 4, SEQ ID No: 5, or SEQ ID No:33.

Any penetration enhancer may be used in the compositions of the invention. In certain embodiments, the penetration enhancer is a peptide or peptidomimetic linked to a protective group. Peptides suitable for use in the invention may contain any known amino acids, including natural amino acids, non-natural amino acids, D-amino acids, and amino-acid derivatives. In a particular embodiment, the penetration enhancer is a peptide selected from the group consisting of Pro-Leu-Gly-Pro-Arg [SEQ ID NO: 28], Pro-Leu-Gly-Pro-Lys [SEQ ID NO: 29], Pro-Leu-Gly-Pro-Glu [SEQ ID NO: 30], Pro-Leu-Gly-Pro-Asp [SEQ ID NO: 31], Pro-Leu-Gly-Pro [SEQ ID NO: 32], Pro-Leu-Gly and Pro-Leu, N-terminally linked to a protective group such as 4-phenylazobenzyloxycarbonyl (Pz), N-methyl, t-butyloxcarbonyl (t-Boc), fluoroenylmethyloxycarbonyl (FMOC), and carbobenzoxy (CBZ) (see e.g. U.S. Pat. No. 5,534,496, which is hereby incorporated by reference). In a preferred embodiment, the penetration enhancer is Pro-Leu-Gly-Pro-Arg [SEQ ID NO: 28] N-terminally linked to a Pz or FMOC group (see e.g. U.S. Pat. No. 5,534,496, which is hereby incorporated by reference).

It is contemplated within the scope of the invention that the penetration enhancers and antigen-binding proteins may co-delivered to a target tissue in a single pharmaceutical composition, or their delivery may be temporally separated by administration in distinct compositions.

It is further contemplated within the scope of the invention that a penetration enhancer may be conjugated to an antigen-binding protein. All modes of physical or chemical conjugation known in the art are contemplated. For conjugating a chemical group to an amino acid, amino acid derivative, or amino acid mimetic, any suitable chemistry known in the art may be employed. Conjugation may be to any amino acid residue of an antigen-binding protein, including Lysine, Cysteine and Histidine residues.

In certain embodiments, the compositions of the invention may comprise additional compounds suitable for co-delivery with the above-mentioned antigen-binding proteins. Such drugs include, but are not limited to, small molecules, nootropics, polypeptides, and oligonucleotides.

The compositions of the invention may be used to deliver antigen-binding proteins across the tight junctions of any biological membrane including, but are not limited to, mucosal epithelium (e.g., nasal epithelium), and corneal tissue. A particularly preferred target membrane is the nasal epithelium because administration of a composition of the invention to the nasal epithelium results in the direct and specific delivery of an antigen-binding protein into the CNS, preferably without first entering the blood stream.

Treatment of CNS Disorders

The compositions of the invention are particularly suited to treating, preventing and or delaying the progression of CNS disorders because such compositions allow for the direct and selective delivery of antigen-binding polypeptides into the CNS via the nasal mucosa. Suitable disorders for treatment with using the compositions of the invention include, but are not limited to, behavioral/cognitive syndromes, headache disorders (e.g. migraine, cluster headache and tension headache), epilepsy, traumatic brain injury, neurodegenerative disorders (e.g., Adrenoleukodystrophy, Alcoholism, Alexander's disease, Alper's disease, Alzheimer's disease, Amyotrophic lateral sclerosis (also known as Lou Gehrig's Disease), Ataxia telangiectasia, Batten disease (also known as Spielmeyer-Vogt-Sjögren-Batten disease), Bovine spongiform encephalopathy, Canavan disease, Cerebral palsy, Cockayne syndrome, Corticobasal degeneration, Creutzfeldt-Jakob disease, Familial Fatal Insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Sub-acute combined degeneration of spinal cord secondary to Pernicious Anaemia, Spinocerebellar ataxia, Spinal muscular atrophy, Steele-Richardson- Olszewski disease, Tabes dorsalis, and Toxic encephalopathy, cerebrovascular disease (e.g. transient ischemic attack and stroke), sleep disorders, cerebral palsy, infections (e.g. encephalitis, meningitis, and myelitis), neoplasms (e.g. brain and spinal cord tumors), movement disorders (e.g. hemiballismus, tic disorder, and Gilles de la Tourette syndrome), demyelinating diseases of the CNS (e.g. multiple sclerosis Guillain-Barré syndrome, and chronic inflammatory demyelinating polyneuropathy), disorders of peripheral nerves (e.g. myopathy and neuromuscular junctions), altered mental status (e.g. encephalopathy, stupor, and coma), speech and language disorders, paraneoplastic neurological syndromes, and syndromes having functional neurological symptoms with no apparent physiological cause.

Accordingly, in another aspect the invention provides a method of treating or preventing a disease or disorder of the central nervous system, the method comprising administering to the nasal mucosa of a subject in need of treatment thereof, an effective amount of a composition comprising an antigen-binding polypeptide (e.g., an scFv) and a penetration enhancer (e.g., Pz-peptide) such that the disease or disorder is treated or prevented.

In yet another aspect the invention provides a method of selectively delivering an antigen-binding polypeptide to the central nervous system of a subject, the method comprising contacting a composition comprising an antigen-binding polypeptide (e.g., an scFv) and a penetration enhancer (e.g., Pz-peptide) with the nasal mucosa of a subject, whereby the antigen-binding polypeptide is directly and selectively delivered to the central nervous system.

Target Antigens

The antigen-binding polypeptides used in the methods of the invention may bind to one or more specific target antigens. Suitable target antigens include, but are not limited to, TNF-alpha (e.g. Genbank Accession Numbers: NP_000585.2), amyloid beta (e.g. Genbank Accession Number: NP_000475.1), amyloid beta-derived diffusible ligand receptor (see e.g., WO/2004/031400), monoamine oxidase-B (e.g. Genbank Accession Number: NP_000889.3), L-3,4-dihydroxyphenylalanine decarboxylase (e.g. Genbank Accession Number: NP_000781.1), acetyl-coA carboxylase (e.g. Genbank Accession Number: NP_942131.1), N-methyl-D-aspartate acceptor (also known as GRIN1) (e.g. Genbank Accession Number: NP_000823.4)), GRINA (e.g. Genbank Accession Number: NP_000828.1), GRIN2D (e.g. Genbank Accession Number: NP_000827.2), GRIN2C (e.g. Genbank Accession Number: NP_000826.2), GRIN3B (e.g. Genbank Accession Number: NP 619635.1), GRIN2A (e.g. Genbank Accession Number: NP_000824.1), GRIN2B (e.g. Genbank Accession Number: NP_000825.2), GRIN3A (e.g. Genbank Accession Number: NP 597702.2), histamine H1 Receptor (e.g. Genbank Accession Number: NP_000852.1), muscarinic receptor (also known as CHRM1) (e.g. Genbank Accession Number: NP_000729.2), CHRM2 (NP_000730.1), CHRM3 (NP_000731.1), CHRM4 (NP_000732.2), hypocretin receptor 1 (e.g. Genbank Accession Number: NP_001516.2), hypocretin receptor 2 (e.g. Genbank Accession Number: NP_001517.2), 5-hydroxytryptamine (also known as HTR1A) (e.g. Genbank Accession Number: NP_000515.2), dopamine receptor (also known as DRD1) (e.g. Genbank Accession Number: NP_000785.1), DRD2 (e.g. Genbank Accession Number: NP_000786.1), DRD3 (e.g. Genbank Accession Number: NP_000787.2), DRD4 (e.g. Genbank Accession Number: NP_000788.2), DRD5 (e.g. Genbank Accession Number: NP_000789.1), norepinephrine transporter (NET) (e.g. Genbank Accession Number: NP_001034.1), adrenergic beta 1 receptor (e.g. Genbank Accession Number: NP_000675.1), and dopamine D2 receptor (e.g. Genbank Accession Number: NP_000786.1).

Formulations

Another aspect of the invention pertains to pharmaceutical formulations of the antigen-binding polypeptide/penetration enhancer compositions of the invention. Such formulations typically comprise one or more antigen-binding polypeptide, one or more penetration enhancer, and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for, for example, intravenous, intramuscular, subcutaneous, topical (e.g., to eye, skin, or epidermal layer), inhalation, parenteral, spinal or epidermal administration (e.g., by injection or infusion). Depending on the route of administration, the antigen-binding polypeptide/penetration enhancer composition may be coated in a material to protect the compounds from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds may also be incorporated into the compositions.

Pharmaceutical compositions typically must be sterile and stable under the conditions of manufacture and storage. The composition may be formulated as a solution, microemulsion, liposome, or other ordered structure suitable to high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions may be brought about by including in the composition an agent that delays absorption, for example, monostearate salts and gelatin.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient that may be combined with a carrier material to produce a single dosage form will vary depending upon the subject being treated, and the particular mode of administration. The amount of active ingredient that may be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Another aspect of the invention is a method of administering the pharmaceutical compositions of the invention. It is contemplated within the scope of the invention that representative delivery regimens may include oral parenteral (including subcutaneous, intramuscular, and intravenous), rectal, buccal, sublingual, pulmonary, transdermal, intranasal, and oral. The preferred delivery regimen is nasal.

For nasal administration, either a solid or a liquid carrier may be used. The solid carrier includes a coarse powder having particle size in the range of, for example, from about 20 to about 500 microns and such formulation is administered by rapid inhalation through the nasal passages. Where the liquid carrier is used, the formulation may be administered as a nasal spray or drops and may include oil or aqueous solutions of the active ingredients.

Formulations suitable for nasal administration are presented such that particles containing an active compound and desirably having a diameter in the range of 0.5 to 7 microns are delivered in the bronchial tree of the recipient. As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension. Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 ls, upon each operation thereof. As a further possibility an active compound may be in the form of a solution or suspension for use in an atomizer or nebuliser whereby an accelerated airstream or ultrasonic agitation is employed to produce a fine droplet mist for inhalation. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Use of the Compositions

The compositions of the present invention may be used as a medicament, for example for the treatment, prevention and/or delay of progression of a neurological disorder. Accordingly, the composition disclosed herein may be used for the manufacture of a medicament useful for the treatment or prevention of a neurological disorder.

In a preferred embodiment, such a disorder is selected from the group consisting of migraine, depression, Alzheimer's disease, Parkinson's disease, schizophrenia, epilepsy, stroke, meningitis, amyotrophic lateral sclerosis, insomnia, meningitis, memory impairment, multiple sclerosis, narcolepsy, stroke, traumatic brain injury, and stress.

Preferably, the composition is formulated for intranasal delivery.

EXAMPLES

The present disclosure is further illustrated by the following examples, which should not be construed as further limiting.

In general, the practice of the present invention employs, unless otherwise indicated, conventional techniques of chemistry, molecular biology, recombinant DNA technology, and immunology (especially, e.g., immunoglobulin technology). See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); Current Protocols in Molecular Biology, eds. Ausubel et al., John Wiley & Sons (1992). See also, e.g., Polytherics U.S. Pat. No. 6,803,438; EP1701741A2; EP1648518A2; WO05065712A2; WO05007197A2; EP1496941A1; EP1222217B1; EP1210093A4; EP1461369A2; WO03089010A1; WO03059973A2; and EP1210093A1); Genentech US20070092940A1 and EP1240337B1; and ESBATech U.S. Ser. No. 60/899,907, PCT/CH2009/000225, PCT/CH2009/000222, PCT/CH2009/000222, WO 06/131013 and WO03097697A2.

Purification of ESBA105

ESBA105, an anti-TNF-alpha single chain antibody fragment with a molecular weight of 26.3 kDa, was purified from *Escherichia coli* host cells as previously described (Furrer et al. (2009) Invest Opthalmol Vis Sci 50, 771-778; Ottiger et al. (2009) Invest Opthalmol V is Sci 50, 779-786). Briefly, ESBA105 was produced by recombinant expression in *E. coli* BL21(DE3), refolding from inclusion bodies, and subsequent size-exclusion chromatography. For animal studies ESBA105 was formulated at 10 mg/ml (for intranasal administration) or 0.5 mg/ml (for intravenous injection) in 50 mM sodium phosphate, 150 mM NaCl, pH 6.5. The endotoxin content as determined in the LAL clotting assay was below 0.1 EU in all formulations used for in vivo experiments.

Intranasal Administration of Evans Blue

Optimal conditions for targeting proteins to the CNS were initially determined by administering 0.3% Evans blue in 0.9% NaCl via an intranasal route to Balb/c mice. Animals were then sacrificed by $CO_2$ inhalation, at predefined time points, and their lungs and stomachs were harvested and visually inspected for the presence of Evans blue. Optimal conditions were obtained by keeping the animals under isoflurane (Provet, Lyssach, Switzerland) anaesthesia in a supine position and treating each nare with 2 µl Evans blue at five minute intervals until a total of 40 µl was reached (45 min) (Table 1). Consequently, this protocol was used for intranasal administration of ESBA105 in all embodiments described herein.

Intranasal and Intravenous Administration of ESBA105

Prebleeds of all animals were collected ten days before the intranasal or intravenous dosing with ESBA105. Intranasal administration of ESBA105 was carried out under isoflurane (Provet, Lyssach, Switzerland) anaesthesia. Mice were placed in a supine position and a total of 40 µl (400 µg) ESBA105 was administered by pipette in 2 µl drops, treating each nare every five minutes over a total of 45 minutes. For the intranasal PK study, four animals were sacrificed at 1, 2, 4, 6, 8, 10, 12, and 24 hours after the first intranasal instillation. In some experiments 3 mM Pz-peptide (4-Phenylazobenzoxycarbonyl-Pro-Leu-Gly-Pro-D-Arg; Bachem, Bubendorf, Switzerland), a penetration enhancer that facilitates the transport of paracellular markers by triggering opening of tight junctions in a transient, reversible manner (Yen and Lee (1994) Journal of Controlled Release 28, 97-109), was added to the ESBA105 formulation. Four animals were sacrificed at 1, 2, and 4 hours after the first administration. For intravenous injection, mice were placed in a restrainer and 40 µg (80 µl) ESBA105 were injected into the tail vein. The intravenous dose was chosen to best approximate the systemic exposure according to the area under the blood concentration-time curve (AUC) observed over a 4 hour period with intranasal administration of 400 µg ESBA105. Two animals were sacrificed at each time point (1, 2, and 4 hours). At time of sacrifice mice were deeply anaesthetized with a mixture of ketamine (Ketaso1100, 65 mg/kg; Pharmacy, Schlieren, Switzerland), xylazine (Rompun, 13 mg/kg; Provet, Lyssach, Switzerland) and acepromazine (Prequillan, 2 mg/kg; Arovet, Zollikon, Switzerland). A blood sample was collected by heart puncture before perfusing the mice with 20 ml PBS. The brains were carefully harvested and dissected into olfactory bulb, cerebrum including thalamus and hypothalamus, cerebellum and brainstem. The tissues were weighed, frozen on dry ice and stored at −80° C. until analysis.

Tissue Preparation

Tissues were prepared for analysis as follows. 100 µl lysis buffer (10 mM Tris, pH 7.4, 0.1% SDS, with proteinase inhibitor cocktail (Roche Diagnostics, Rotkreuz, Switzerland)) was added to 15 mg of brain tissue. Tissues were sonicated for 5 seconds (8 cycles, 100% intensity) (Sonoplus, Bandelin, Berlin, Germany), centrifuged, and the supernatants were subjected to ELISA based determination of ESBA105 concentrations.

Quantification of ESBA105 in Serum and Brain Tissue

ESBA105 concentrations were determined by triplicate measurements of each sample in a direct ELISA. 96-well plates (NUNC MaxiSorp; Omnilab, Mettmenstetten, Switzerland) were coated with 0.5 µg/ml human TNF-alpha (Peprotech, London, UK) in PBS overnight at 4° C. Between each of the following steps plates were washed three times with TBS-T (0.005% Tween20; Axon Lab, Baden-Dattwyl, Switzerland) using a micro plate washer (ASYS Atlantis, Salzburg, Austria). Unspecific binding sites were saturated by 1.5 hour incubation in PBS/1% BSA/0.2% Tween20. Predilutions of each sample were prepared in dilution buffer (PBS, 0.1% BSA, 0.2% Tween20) containing 10% of the respective matrix (olfactory bulb, cerebrum, cerebellum, brainstem or serum). Standard reference dilution series (50-0.5 ng/ml) of ESBA105 were prepared in dilution buffer/10% respective matrix. Prediluted samples and standard reference dilutions were then added to the wells and plates were incubated for 1.5 hours at room temperature. Bound ESBA105 was detected with a biotinylated affinity purified polyclonal rabbit anti-ESBA105 antibody (AK3A, ESBATech, Schlieren, Switzerland) that was diluted 1:20'000 in dilution buffer (1.5 h, room temperature). AK3A, in turn, was detected with poly-horseradish peroxidase streptavidin (Stereospecific Detection Technologies, Baesweiler, Germany) at a concentration of 0.2 ng/ml dilution buffer. POD (Roche Diagnostics, Rotkreuz, Switzerland) was used as peroxidase substrate and the color reaction was stopped after 2 to 20 minutes (depending on color intensity) by addition of 1 M HCl. Absorbance was measured at 450 nm in a plate reader (Sunrise; Tecan, Maennedorf, Switzerland) and ESBA105 concentrations in samples were calculated by polynomial regression from a standard curve (GraphPad Prism 4.03; GraphPad Software, Inc., San Diego, Calif.). The minimum quantifiable concentration (LOQ) of ESBA105 was 5 ng/ml in serum and 33 ng/ml in brain tissue, respectively. Undiluted samples that resulted in signals below the lower limit of quantitation were set to LOQ for mathematical evaluation and graphical display.

Example 1

Mode of Intranasal Administration

This example demonstrates that low volume nasal administration results in specific delivery to the CNS. For efficient and specific drug delivery into the CNS, an applied substance should remain in the nasal cavity; however, several studies have shown that an intranasally applied substance may migrate to the respiratory system and the gastrointestinal tract due to breathing and ingestion (Eyles et al. (1999) Int J Pharm 189, 75-79; Klavinskis et al. (1999) J Immunol 162, 254-262; Lundholm et al. (1999) Vaccine 17, 2036-2042; Trolle et al. (2000) Vaccine 18, 2991-2998). One of skill in the art will appreciate that a number of aspects (e.g. anesthesia, animal position, and volume and frequency of administration) may influence the residence time of the administered compound in the nasal cavity. Using the intranasal administration protocol described above, Evans Blue was used as a tracer to assess the post-administration distribution of the dye after intranasal application. 40-50 μl Evans blue was administered intranasally via several different methods. First, a single dose was given to either anaesthetized or alert mice held in a supine position, which resulted in dye migrating to both the lungs and stomach in both cases. Second, a single dose was given to anaesthetized animals for 30-50 minutes in the supine position instead of only 3 minutes. Third, the volume of die was administered in two separate 10 μl doses that were administered at 5 minutes intervals. Neither of these methods reduced Evans blue migration to the lungs and stomach. Finally, volumes as low as 2 μl were applied to anaesthetized animals in the supine position, which resulted in only minimal traces of Evans blue in the lungs and blue staining was totally absent in the stomach (Table 1).

Example 2

Delivery of ESBA105 to the CNS

This example demonstrates that intranasal administration of a scFv results in delivery of the scFv to the CNS. ESBA105 (SEQ ID NO: 1) is a single chain antibody that specifically binds and inhibits TNFalpha (see e.g. WO 06/131013, which is hereby incorporated by reference). Following intranasal administration by the above described protocol, ESBA105 reached significant concentrations in all regions of the brain analyzed, and displayed a bimodal distribution over time. Maximum ESBA105 concentrations ($C_{max}$) in cerebellum and brainstem were reached one hour after the first instillation, with concentrations in the olfactory bulb and cerebrum peaking one hour later. ESBA105 levels then declined in all brain regions, but rose again after 6-12 hours to produce a clear second, lower level, concentration peak in the olfactory bulb, cerebellum, and brainstem (FIG. 1), which demonstrates that two different migration routes are likely to exist. Highest concentrations were measured in the olfactory bulb and the brainstem. In the olfactory bulb, which is connected to the nasal cavity through the olfactory system (*N. olfactorius*), concentrations culminated at 9455 ng/ml. Concentrations were even higher in the brainstem (11067 ng/ml), which is connected to the nasal passages through the peripheral trigeminal system (*N. trigeminus*) (Table 2). $C_{max}$ in the cerebrum (975 ng/ml) was slightly delayed (2 hours), and about seven to ten times lower than in the cerebellum or the olfactory bulb, respectively. These results demonstrate that ESBA105 first reaches the olfactory bulb and the brainstem and from there distributes to cerebrum and cerebellum. Similar to the brainstem and cerebellum, $C_{max}$ in serum was reached at one hour after the first administration of ESBA105 and peaked a second time between five and 10 hours. Interestingly, ESBA105 levels remained almost constant during the last 12 hours (FIG. 1).

Example 3

ESBA105 Delivery to the CNS is Direct

This example demonstrates that intranasal administration of ESBA105 results in direct delivery to the CNS, rather than via the bloodstream. To determine whether ESBA105 migrates directly through the BBB to the CNS from the nasal cavity, or indirectly via systemic absorption and subsequent trans-BBB delivery to the brain, intranasal administration was compared side by side with intravenous injection as described above. Following intravenous injection, considerable concentrations of ESBA105 were reached in all analyzed regions, except the cerebrum where concentrations were below the lower limit of quantitation. However, considerably higher drug concentrations were measured in all brain regions following intranasal administration (FIG. 2). Maximum ESBA105 levels in cerebellum and brainstem upon intranasal dosing were about 10-18 fold higher than those following intravenous injection. Moreover, $C_{max}$ in the olfactory bulb was more than 60-fold higher for intranasal versus intravenous administration (Table 3). Surprisingly, although dosing was set to produce similar systemic exposures for both routes, serum concentrations were clearly lower after intranasal administration (FIG. 2), reaching 6006 ng/ml while $C_{max}$ following intravenous injection was more than 10-fold higher (63709 ng/ml) (Table 3). Following intravenous injection, maximal concentrations ($C_{max}$) and exposures (AUC) in olfactory bulb, cerebellum and brainstem reached similar values with 202, 257, and 174 ng/ml for $C_{max}$ and 448, 567, and 416 ng-h/ml for AUC, respectively. $C_{max}$ in brain tissues following intravenous injection was at 2 hours and no ESBA105 could be detected at 4 hours. In contrast, following intranasal administration clearly higher concentrations were measured in all brain regions. Highest values were obtained for the olfactory bulb ($C_{max}$: 12586 ng/ml; AUC: 23130 ng-h/ml) followed by brainstem ($C_{max}$: 3169 ng/ml; AUC: 7942 ng-h/ml), cerebellum ($C_{max}$: 2819 ng/ml; AUC: 5908 ng-h/ml) and cerebrum ($C_{max}$: 1831 ng/ml; AUC: 2951 ng-h/ml). Moreover, in contrast to intravenous injection, there were still detectable concentrations of ESBA105 in all brain regions four hours after intranasal administration. These results demonstrate that ESBA105 is able to penetrate from the blood across the BBB into the CNS, and that the most efficient route of delivery is via intranasal administration (Table 3).

Example 4

Pz-Peptide Improves ESBA105 Delivery Across the BBB

This example demonstrates that the Pz-peptide significantly enhances the intranasal delivery of a scFv to the CNS. Specifically, the ability of the Pz-peptide to function as a penetration enhancer for transport of drugs through the BBB was examined by adding 3 mM Pz-peptide to ESBA105 and assessing transport to the brain. In presence of Pz-peptide, $C_{max}$ in olfactory bulb, cerebrum and cerebellum was reached earlier than ESBA105 alone (one instead of two hours after first dosing) (Table 4). Furthermore, addition of Pz-peptide resulted in a 2- to 3-fold increase in $C_{max}$ in olfactory bulb and cerebrum (7309 to 15786 ng/ml and 1133 to 3417 ng/ml, respectively), while $C_{max}$ in the brainstem remained unchanged. Tissue-to-blood ratios for $C_{max}$ were clearly higher in olfactory bulb and cerebrum with co-administration of ESBA105 and Pz-peptide than with ESBA105 alone (FIG. 3A). The effect on delivery to cerebellum, brainstem and serum was, however, less pronounced. In summary, Pz-peptide can enhance delivery of large molecular weight proteins to the olfactory bulb and the cerebrum without increasing systemic exposure (FIG. 3). Therefore, for therapeutic applications, Pz-peptide may enhance drug delivery without increasing the risk of systemic side effects (Table 4).

TABLE 1

Administration scheme and presence of dye following intranasal delivery of 0.3% Evans blue dye.

| application | | | anaesthesia | | sacrificed (after first | Evans blue | |
|---|---|---|---|---|---|---|---|
| volume | interval | nare | isoflurane | duration | administration) | lungs | stomach |
| 1 × 40 μl | — | both | no | — | 50 min | + | ++ |
| 1 × 40 μl | — | both | yes | 3 min | 50 min | + | (+) |
| 1 × 50 μl | — | both | yes | 3 min | 3 min | + | + |
| 1 × 50 μl | — | both | yes | 3 min | 30 min | ++ | ++ |
| 1 × 50 μl | — | both | yes | 3 min | 50 min | ++ | ++ |
| 10 × 10 μl | 5 min | alternating | yes | 45 min | 55 min | +++ | +++ |
| 10 × (2 + 2 μl) | 5 min | 2 μl per nare | yes | 45 min | 50 min | – | – |

TABLE 2

Pharmacokinetic parameters after intranasal administration of 400 μg ESBA105.

| | $C_{max}$ | | | | |
|---|---|---|---|---|---|
| | ng/ml | ng/mg of total protein | $T_{max}$ hours | AUC ng-h/ml | AUC/mg ng-h/ml |
| Olfactory bulb | 9455 ± 6465 | 10459 ± 7152 | 2 | 51913 | 129'782 |
| Cerebrum | 975 ± 1806 | 1079 ± 1998 | 2 | 2576 | 6'440 |
| Cerebellum | 7354 ± 8240 | 8134 ± 9115 | 1 | 13249 | 33'123 |
| Brainstem | 11067 ± 18530 | 12242 ± 20498 | 1 | 21770 | 54'425 |
| Serum | 7191 ± 975 | nd | 1 | 26257 | 65'643 |

TABLE 3

Pharmacokinetic parameters after intranasal or intravenous administration of ESBA105.

| | Intranasal[a] | | | | Intravenous[a] | | | | $AUC_{(in)}$/ |
|---|---|---|---|---|---|---|---|---|---|
| | $C_{max}$ (ng/ml) | $T_{max}$ (h) | AUC (ng-h/ml) | AUC/mg[b] (ng-h/ml) | $C_{max}$ (ng/ml) | $T_{max}$ (h) | AUC (ng-h/ml) | AUC/mg[b] (ng-h/ml) | $AUC_{(iv)}$ (per mg) |
| Olf. bulb | 12586 ± 24693 | 2 | 23130 | 57825 | 202 ± 238 | 2 | 448 | 11200 | 5.16 |
| Cerebrum | 1831 ± 3476 | 2 | 2951 | 7378 | 0 | nd | 0 | nd | nd |
| Cerebellum | 2819 ± 3830 | 2 | 5908 | 14770 | 257 ± 316 | 2 | 567 | 14175 | 1.04 |
| Brainstem | 3169 ± 2211 | 1 | 7942 | 19855 | 174 ± 28 | 2 | 416 | 10400 | 1.91 |
| Serum | 6006 ± 1896 | 2 | 15709 | 39273 | nd | nd | 54254 | 1356350 | 0.03 |
| Cerebrum[c] | 1831 ± 3476 | 2 | 2951 | 7378 | 142 ± 126 | 2 | 375 | 938 | 7.87 |

[a]The doses of 400 μg (intranasal) and 40 μg (intravenous) were chosen to reach a similar systemic exposure.

[b]AUC normalized to 1 mg assuming that the AUC increases linearly with different doses.

[c]Intranasal or intravenous administration of an equal dose of EBSA105 (400 μg).

TABLE 4

Pharmacokinetic parameters after intranasal delivery of 400 μg ESBA105 with or without 3 mM Pz-peptide.

| | ESBA105 | | | ESBA105/Pz-peptide | | | | |
|---|---|---|---|---|---|---|---|---|
| | $C_{max}$ (ng/ml) | $T_{max}$ (h) | AUC (ng·h/ml) | $C_{max}$ (ng/ml) | $T_{max}$ (h) | AUC (ng·h/ml) | $C_{maxE105}/C_{maxE105/Pz}$ | $AUC_{E105}/AUC_{E105/Pz}$ |
| Olf. bulb | 7309 ± 17233 | 2 | 16854 | 15786 ± 29556 | 1 | 22210 | 0.46 | 0.76 |
| Cerebrum | 1133 ± 2403 | 2 | 2792 | 3417 ± 7832 | 1 | 4303 | 0.33 | 0.65 |
| Cerebellum | 1714 ± 2796 | 2 | 3922 | 2119 ± 2355 | 1 | 4367 | 0.81 | 0.90 |
| Brainstem | 1850 ± 2053 | 1 | 4578 | 3454 ± 2818 | 1 | 4157 | 0.54 | 1.10 |
| Serum | 4645 ± 2422 | 2 | 12656 | 4109 ± 2943 | 2 | 12010 | 1.13 | 1.05 |

TABLE 5 scFv, VH, and VL sequences

| SEQ ID NO: | Name: | Sequence: |
|---|---|---|
| 1 | ESBA105 scFv (α-TNFalpha) / WO 2006/131013 | MADIVMTQSPSSLSASVGDRVTLTCTASQSVSNDVVWYQ QRPGKAPKLLIYSAFNRYTGVPSRFSGRGYGTDFTLTIS SLQPEDVAVYYCQQDYNSPRTFGQGTKLEVKRGGGGSGG GGSGGGGSSGGGSQVQLVQSGAEVKKPGASVKVSCTASG YTFTHYGMNWVRQAPGKGLEWMGWINTYTGEPTYADKFK DRFTFSLETSASTVYMELTSLTSDDTAVYYCARERGDAM DYWGQGTLVTVSS |
| 2 | EP34max scFv (α-TNFalpha) | EIVMTQSPSTLSASLGDRVIITCQSSQSVYGNIWMAWYQ QKSGKAPKLLIYQASKLASGVPSRFSGSGSGAEFSLTIS SLQPDDFATYYCQGNFNTGDRYAFGQGTKLTVLGGGGGS GGGGSGGGGSGGGGSEVQLVESGGGLVQPGGSLRLSCTA SGFTISRSYWICWVRQAPGKGLEWVACIYGDNDITPLYA NWAKGRFPVSTDTSKNTVYLQMNSLRAEDTAVYYCARLG YADYAYDLWGQGTLVTVSS |
| 3 | EP43max scFv (α-TNFalpha) | EIVMTQSPSTLSASVGDRVIIKCQASQSISDWLAWYQQK PGKAPKLLIYGASRLASGFPSRFSGSGSGAEFTLTISGL EPADFATYYCQQGWSDSYVDNLFGQGTKLTVLGGGGGSG GGGSGGGGSGGGGSEVQLVESGGGLVQPGGSLRLSCTVS GFSLSSGAMSWVRQAPGKGLEWVGVIISSGATYYASWAK GRFTISKDTSKNTVYLQMNSLRAEDTAVYYCARGGPDDS NSMGTFDPWGQGTLVTVSS |
| 4 | ESBA212 scFv VL (α-Abeta) / WO 2009/033309 | ADIVLTQSPSSLSASVGDRVTLTCRASSSVNYMHWYQQR PGKPPKALIYATSNLASGVPSRFSGSGSGTEFTLTISSL QPEDVAVYYCQQWRTNPPTFGQGTKLEVKRGGGGSGGGG SGGGGSGGGGSQVQLVQSGPEVKKPGASVKVSCTASGYT FTEYTMHWVRQAPGQGLEWMGGVNPYNDNTSYIRKLQGR VTLTVDRSSSTAYMELTSLTSDDTAVYYCARYGGLRPYY FPMDFWGQGTLVTVSS |
| 5 | ESBA521 scFv (α-ALK1) / WO 2007/124610 | QSVLTQPPSVSAAPGQKVTISCSGSTSNIGDNYVSWYQQ LPGTAPQLLIYDNTKRPSGIPDRFSGSKSGTSATLGITG LQTGDEADYYCGTWDSSLSGVVFGGGTKLTVLGGGGGSG GGGSGGGGSSGGGSEVQLVESGGGLVQPGGSLRLSCAAS GFTFSSYAMSWVRQAPGKGLEWVSAISGSGGSTYYADSV KGRFTISRDNSKNTLYLQMNSLRAEDTAVYYCARDAGIA VAGTGFDYWGQGTLVTVSS |
| 33 | ESBA903 scFv (α-VEGF) | EIVMTQSPSTLSASVGDRVIITCQASEIIHSWLAWYQQK PGKAPKLLIYLASTLASGVPSRFSGSGSGAEFTLTISSL QPDDFATYYCQNVYLASTNGANFGQGTKLTVLGGGGGGS GGGGSGGGGSSGGGSEVQLVESGGGLVQPGGSLRLSCTA SGFSLTDYYYMTWVRQAPGKGLEWVGFIDPDDDPYYATW AKGRFTISRDTSKNTVYLQMNSLRAEDTAVYYCAGGDHN SGWGLDIWGQGTLVTVSS |
| 6 | ESBA105 VH | QVQLVQSGAEVKKPGASVKVSCTASGYTFTHYGMNWVRQ APGKGLEWMGWINTYTGEPTYADKFKDRFTFSLETSAST VYMELTSLTSDDTAVYYCARERGDAMDYWGQGTLVTVSS |
| 7 | EP34max VH | EVQLVESGGGLVQPGGSLRLSCTASGFTISRSYWICWVR QAPGKGLEWVACIYGDNDITPLYANWAKGRFPVSTDTSK NTVYLQMNSLRAEDTAVYYCARLGYADYAYDLWGQGTLV TVSS |

TABLE 5-continued scFv, VH, and VL sequences

| SEQ ID NO: | Name: | Sequence: |
|---|---|---|
| 8 | EP43max VH | EVQLVESGGGLVQPGGSLRLSCTVSGFSLSSGAMSWVRQAPGKGLEWVGVIISSGATYYASWAKGRFTISKDTSKNTVYLQMNSLRAEDTAVYYCARGGPDDSNSMGTFDPWGQGTLVTVSS |
| 9 | ESBA212 VH | QVQLVQSGPEVKKPGASVKVSCTASGYTFTEYTMHWVRQAPGQGLEWMGGVNPYNDNTSYIRKLQGRVTLTVDRSSSTAYMELTSLTSDDTAVYYCARYGGLRPYYFPMDFWGQGTLVTVSS |
| 10 | ESBA521 VH | EVQLVESGGGLVQPGGSLRLSCAASGFTFSSYAMSWVRQAPGKGLEWVSAISGSGGSTYYADSVKGRFTISRDNSKNTLYLQMNSLRAEDTAVYYCARDAGIAVAGTGFDYWGQGTLVTVSS |
| 35 | ESBA903 VH | EVQLVESGGGLVQPGGSLRLSCTASGFSLTDYYYMTWVRQAPGKGLEWVGFIDPDDDPYYATWAKGRFTISRDTSKNTVYLQMNSLRAEDTAVYYCAGGDHNSGWGLDIWGQGTLVTVSS |
| 11 | ESBA105 VL | MADIVMTQSPSSLSASVGDRVTLTCTASQSVSNDVVWYQQRPGKAPKLLIYSAFNRYTGVPSRFSGRGYGTDFTLTISSLQPEDVAVYYCQQDYNSPRTFGQGTKLEVKR |
| 12 | EP34max VL | EIVMTQSPSTLSASLGDRVIITCQSSQSVYGNIWMAWYQQKSGKAPKLLIYQASKLASGVPSRFSGSGSGAEFSLTISSLQPDDFATYYCQGNFNTGDRYAFGQGTKLTVL |
| 13 | EP43max VL | EIVMTQSPSTLSASVGDRVIIKCQASQSISDWLAWYQQKPGKAPKLLIYGASRLASGFPSRFSGSGSGAEFTLTISGLEPADFATYYCQQGWSDSYVDNLFGQGTKLTVLG |
| 14 | ESBA212 | ADIVLTQSPSSLSASVGDRVTLTCRASSSVNYMHWYQQRPGKPPKALIYATSNLASGVPSRFSGSGSGTEFTLTISSLQPEDVAVYYCQQWRTNPPTFGQGTKLEVKR |
| 15 | ESBA521 VL | QSVLTQPPSVSAAPGQKVTISCSGSTSNIGDNYVSWYQQLPGTAPQLLIYDNTKRPSGIPDRFSGSKSGTSATLGITGLQTGDEADYYCGTWDSSLSGVVFGGGTKLTVLG |
| 34 | ESBA903 VL (α-VEGF) | EIVMTQSPSTLSASVGDRVIITCQASEIIHSWLAWYQQKPGKAPKLLIYLASTLASGVPSRFSGSGSGAEFTLTISSLQPDDFATYYCQNVYLASTNGANFGQGTKLTVLG |

TABLE 6

Linker Sequences

| SEQ ID NO: | Modified (MLS) and Standard (SLS) Linker Sequence Name: | Sequence: |
|---|---|---|
| 16 | MLS 1 | GGGGSGGGGSCGGGSGGGCGGGGSGGGGS |
| 17 | MLS 2 (Pep1) | GGGGSGGGGSCGAHWQFNALTVRCGGGGSGGGS |
| 18 | MLS 3 | GGGGSGGGGSC(X)$_{3-50}$CGGGGSGGGGS |
| 19 | MLS 4 | (X)$_{3-15}$C(X)$_{3-50}$CG(X)$_{3-15}$ |
| 36 | SLS 1 | GGGGSGGGGSGGGGSGGGGS |
| 37 | SLS 2 | GGGGSGGGGSGGGGSSGGGS |

TABLE 7

Framework Sequences

| SEQ ID NO: | Framework Name: | Sequence: |
|---|---|---|
| 20 | FW1.4 VH (a43) | EVQLVESGGGLVQPGGSLRLSCAAS(X)$_{n=1-50}$WVRQAPGKGLEWVS(X)$_{n=1-50}$RFTISRDNSKNTLYLQMNSLRAEDTAVYYCAK(X)$_{n=1-50}$WGQGTLVTVSS |
| 21 | FW1.4 VL (KI27) | EIVMTQSPSTLSASVGDRVIITC(X)$_{n=1-50}$WYQQKPGKAPKLLIY(X)$_{n=1-50}$GVPSRFSGSGSGAEFTLTISSLQPDDFATYC(X)$_{n=1-50}$FGQGTKLTVLG |
| 22 | FW1.4 scFv | EIVMTQSPSTLSASVGDRVIITC(X)$_{n=1-50}$WYQQKPGKAPKLLIY(X)$_{n=1-50}$GVPSRFSGSGSGAEFTLTISSLQPDDFATYC(X)$_{n=1-50}$FGQGTKLTVLGGGGGSGGGGSGGGGSGGGGSEVQLVESGGGLVQPGGSLRLSCAAS(X)$_{n=1-50}$WVRQAPGKGLEWVS(X)$_{n=1-50}$RFTISRDNSKNTLYLQMNSLRAEDTAVYYCAK(X)$_{n=1-50}$WGQGTLVTVSS |

TABLE 7-continued

Framework Sequences

| SEQ ID NO: | Framework Sequence Name: | Sequence: |
|---|---|---|
| 23 | rFW1.4 VH | EVQLVESGGGLVQPGGSLRLSCTAS(X)$_{n=1-50}$WVRQAPGKGLEWVG(X)$_{n=1-50}$RFTISRDTSKNTVYLQMNSLRAEDTAVYYCAR(X)$_{n=1-50}$WGQGTLVTVSS |
| 24 | rFW1.4 VL = rFW1.4v2 VL | EIVMTQSPSTLSASVGDRVIITC(X)$_{n=1-50}$WYQQKPGKAPKLLIY(X)$_{n=1-50}$GVPSRFSGSGSGTEFTLTISSLQPDDFATYC(X)$_{n=1-50}$FGQGTKLTVLG |
| 25 | rFW1.4 scFv | EIVMTQSPSTLSASVGDRVIITC(X)$_{n=1-50}$WYQQKPGKAPKLLIY(X)$_{n=1-50}$GVPSRFSGSGSGTEFTLTISSLQPDDFATYC(X)$_{n=1-50}$FGQGTKLTVLGGGGGSGGGGSGGGGSGGGGSEVQLVESGGGLVQPGGSLRLSCTAS(X)$_{n=1-50}$WVRQAPGKGLEWVG(X)$_{n=1-50}$RFTISRDTSKNTVYLQMNSLRAEDTAVYYCAR(X)$_{n=1-50}$WGQGTLVTVSS |
| 26 | rFW1.4(V2) VH | EVQLVESGGGLVQPGGSLRLSCTVS(X)$_{n=1-50}$WVRQAPGKGLEWVG(X)$_{n=1-50}$RFTISKDTSKNTVYLQMNSLRAEDTAVYYCAR(X)$_{n=1-50}$WGQGTLVTVSS |
| 27 | rFW1.4(V2) scFv | EIVMTQSPSTLSASVGDRVIITC(X)$_{n=1-50}$WYQQKPGKAPKLLIY(X)$_{n=1-50}$GVPSRFSGSGSGTEFTLTISSLQPDDFATYC(X)$_{n=1-50}$FGQGTKLTVLGGGGGSGGGGSGGGGSGGGGSEVQLVESGGGLVQPGGSLRLSCTVS(X)$_{n=1-50}$WVRQAPGKGLEWVG(X)$_{n=1-50}$RFTISKDTSKNTVYLQMNSLRAEDTAVYYCAR(X)$_{n=1-50}$WGQGTLVTVSS |

TABLE 8

Penetration Enhancer Sequences

| SEQ ID NO: | Sequence: |
|---|---|
| 28 | PLGPR |
| 29 | PLGPK |
| 30 | PLGPE |
| 31 | PLGPD |
| 32 | PLGP |

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. A composition comprising an antigen-binding polypeptide and a penetration enhancer, wherein the antigen-binding polypeptide comprises an amino acid sequence with at least 80% similarity to SEQ ID No: 25.

2. The composition of claim 1, wherein the penetration enhancer is Pz-peptide or FMOC -peptide.

3. The composition of claim 1, wherein the antigen-binding polypeptide is an immunobinder.

4. The composition of claim 3, wherein the immunobinder is an scFv.

5. The composition of claim 1, wherein the antigen-binding polypeptide specifically binds to a target antigen selected from the group consisting of TNF-alpha, amyloid beta, amyloid beta-derived diffusible ligand receptor, monoamine oxidase-B, L-3,4-dihydroxyphenylalanine decarboxylase, acetyl-coA carboxylase, N-methyl-D-aspartate aeceptor (also known as GRIN1), GRINA, GRIN2D, GRIN2C, GRIN3B, GRIN2A, GRIN2B, GRIN3A, histamine H1 Receptor, muscarinic receptor (also known as CHRM1), CHRM2, CHRM3, CHRM4, hypocretin receptor 1, hypocretin receptor 2, 5-hydroxytryptamine (also known as HTR1A), dopamine receptor (also known as DRD1), DRD2, DRD3, DRD4, DRD5, adrenergic beta 1 receptor, norepinephrin transporter (NET), and dopamine D2 receptor.

6. The composition of claim 4, wherein the scFv comprises a VH domain comprising an amino acid sequence with at least 80% similarity to SEQ ID No: 7 or SEQ ID No: 8.

7. The composition of claim 4, wherein the scFv comprises a VL domain comprising an amino acid sequence with at least 85% similarity to SEQ ID No: 12 or SEQ ID No: 13.

8. The composition of claim 4, wherein the scFv comprises an amino acid sequence with at least 80% similarity to SEQ ID No: 2 or SEQ ID No: 3.

9. The composition of claim 4, wherein the scFv further comprises an amino acid sequence with at least 80% similarity to SEQ ID NO: 36.

10. The composition of claim 1, wherein the antigen-binding polypeptide is covalently linked to the penetration enhancer.

11. The composition of claim 1, wherein the penetration enhancer facilitates the selective intranasal delivery of the antigen-binding polypeptide to the central nervous system.

12. A kit comprising an antigen-binding polypeptide of claim 1, a penetration enhancer, and instructions for use.

13. A pharmaceutical composition comprising the composition of claim 1 and a pharmaceutically acceptable carrier.

14. The pharmaceutical composition of claim 13, which is for the treatment or delay of progression of a neurological disorder.

15. The pharmaceutical composition of claim 14, wherein the disorder is selected from the group consisting of migraine, depression, Alzheimer's disease, Parkinson's disease, schizophrenia, epilepsy, stroke, meningitis, amyotrophic lateral sclerosis, insomnia, meningitis, memory impairment, multiple sclerosis, narcolepsy, stroke, traumatic brain injury, and stress.

\* \* \* \* \*